United States Patent
Fillmore et al.

(10) Patent No.: US 6,481,462 B2
(45) Date of Patent: *Nov. 19, 2002

(54) MEDICAL FLUSH VALVE

(75) Inventors: David J. Fillmore, Tulsa, OK (US); Matthew S. Longson, Holliday, UT (US)

(73) Assignee: NeoSci Medical, Inc., Draper, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/798,444

(22) Filed: Mar. 2, 2001

(65) Prior Publication Data

US 2002/0000253 A1 Jan. 3, 2002

Related U.S. Application Data

(63) Continuation-in-part of application No. 09/257,612, filed on Feb. 25, 1999, now Pat. No. 6,240,960.

(51) Int. Cl.$^7$ .............................................. F16K 11/14
(52) U.S. Cl. ........................................ 137/607; 251/7
(58) Field of Search ............................. 137/607, 625.4, 137/597; 251/7; 604/33, 34, 258

(56) References Cited

U.S. PATENT DOCUMENTS

| | | | |
|---|---|---|---|
| 754,760 A | 3/1904 | Fesenfeld | |
| 2,471,623 A | * 5/1949 | Hubell | 137/625.18 |
| 2,474,286 A | 6/1949 | Snyder | 137/111 |
| 3,416,567 A | 12/1968 | Van Dardel et al. | 137/604 |
| 3,699,964 A | 10/1972 | Ericson | 128/275 |
| 3,906,935 A | 9/1975 | Raia et al. | 128/2 F |
| 4,765,367 A | 8/1988 | Scott | 137/607 |
| 5,030,210 A | 7/1991 | Alchas | 604/247 |
| 5,083,561 A | 1/1992 | Russo | 128/207.16 |
| 5,220,916 A | 6/1993 | Russo | 128/207.16 |
| 5,346,470 A | 9/1994 | Hobbs et al. | 604/24 |
| 5,360,412 A | 11/1994 | Nakao et al. | 604/247 |
| 5,549,651 A | 8/1996 | Lynn | 604/283 |
| 5,645,538 A | 7/1997 | Richmond | 604/256 |
| 5,676,136 A | 10/1997 | Russo | 128/205.24 |
| 5,730,727 A | 3/1998 | Russo | 604/118 |
| 5,775,325 A | 7/1998 | Russo | 128/205.12 |
| 6,240,960 B1 | 6/2001 | Fillmore | 137/607 |

* cited by examiner

Primary Examiner—Stephen M. Hepperle
(74) Attorney, Agent, or Firm—Workman, Nydegger & Seeley; John C. Stringham

(57) ABSTRACT

A valve apparatus is provided that includes a housing having proximal and distal ends and defining a passageway therethrough. An access port of the housing defines a bore configured for selective communication with the passageway. The valve apparatus includes a hollow insert which is disposed in the distal end of the passageway and includes a portion that is disposed beneath the bore defined by the access port. The housing additionally includes retention tabs on the distal end that engage corresponding openings in a fitting that is attached to the housing and includes a nipple slidingly received within the insert. A seat on the nipple contacts a flange of the insert to form a substantially leak proof connection. A substantially identical fitting engages corresponding retention tabs on the access port and is configured to slidingly receive a plunger, disposed in the bore, within a passage defined by the nipple. A sealing ring disposed in the bore around the plunger is compressed by the nipple and acts to prevent leakage past the plunger. The plunger is biased upwards out of the passageway, defined by the housing, by the resilience of the insert, so that fluid can readily flow between the proximal and distal ends of the passageway.

34 Claims, 12 Drawing Sheets

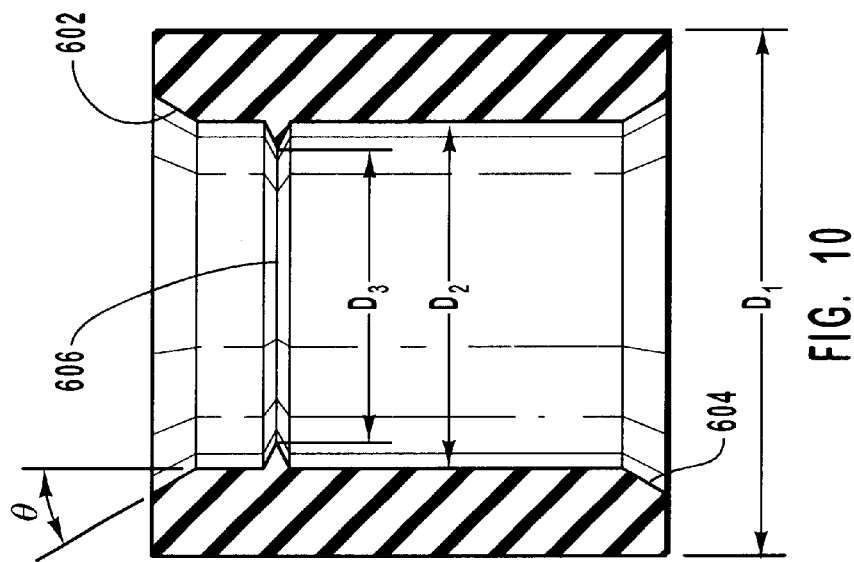
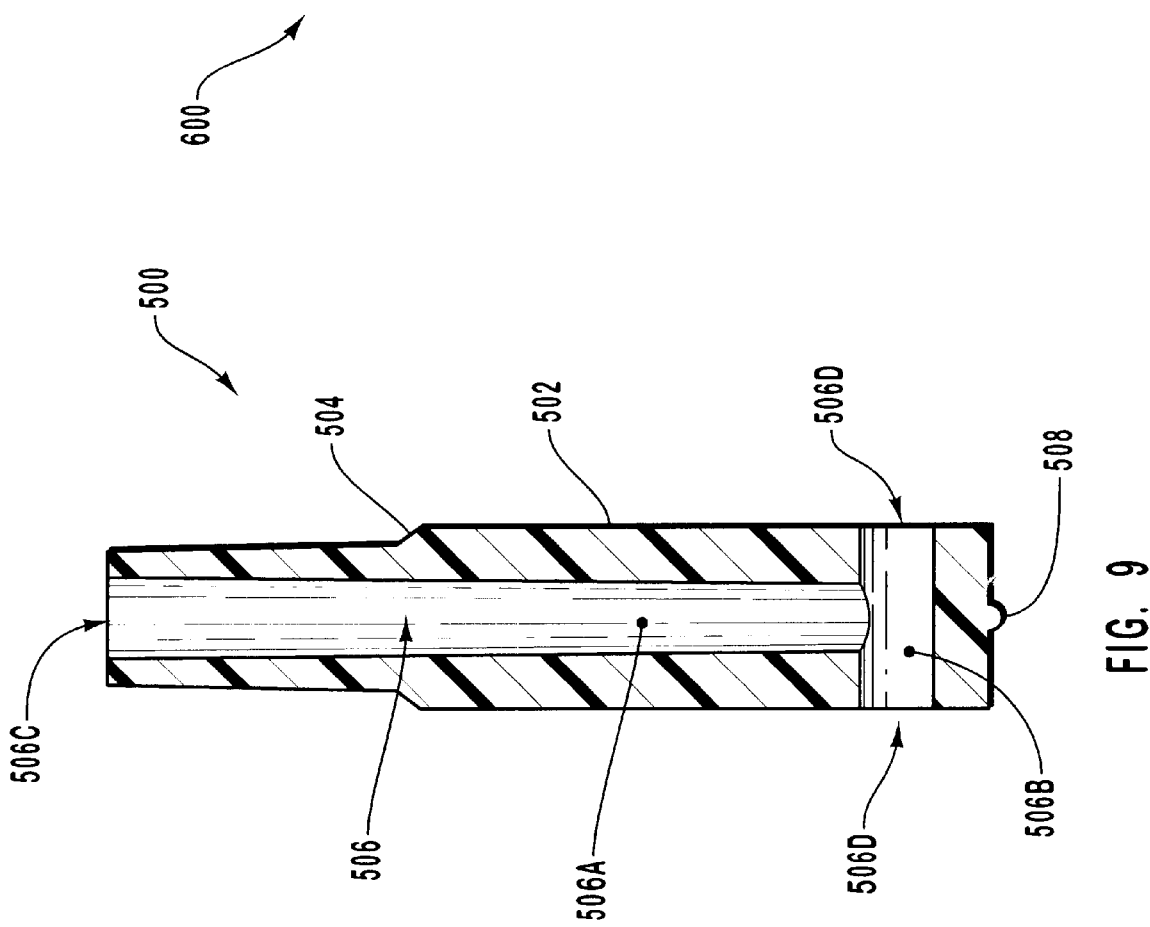

MEDICAL FLUSH VALVE

The Relevant Technology

This application is a continuation-in-part (CIP) of U.S. patent application Ser. No. 09/257,612, entitled *Back Flush Valve For One-Way Flush of Drainage Catheters*, filed Feb. 25, 1999, now U.S. Pat. No. 6,240,960, and incorporated herein in its entirety by this reference.

BACKGROUND OF THE INVENTION

1. The Field of the Invention

The present invention relates generally to devices used to implement various medical procedures. More particularly, embodiments of the present invention relate to an improved valve for use in flushing medical devices and for facilitating the performance of various diagnostic, analytic, therapeutic, and other procedures.

2. The Relevant Technology

In the medical field, tubes and catheters are used in a wide variety of applications including drainage procedures or applications. In these type of applications, the tubes or catheters are of the type which carry various bodily fluids, including but not limited to, abscess fluids, urinary fluids, and biliary fluids. One purpose of such tubes or catheters is to decompress, relieve, or drain a specific collection of fluid from a patient. The expressed fluid is amassed into a collection bag for evaluation or evacuation.

It is important that the interior passageway, or lumen, in drainage tubes and catheters remain unobstructed and that materials such as particulates and/or residues not be allowed to collect or build up on the surface of the lumen in the catheter or tube. The buildup of particulates and/or residues on the interior surface of the lumen in the tube or catheter may lead to uneven, reduced, or obstructed flow. Obstructed, limited, or even uneven fluid flow may extend the recovery time of a patient, resulting in the potential for further complications or infections. For example, an obstructed catheter could cause an infection in the patient that may result, in some cases, in the sickness or even death of the patient. These problems are exacerbated in situations where catheters or tubes which are kept in place for longer periods of time.

In order to avoid such problems, the tubes or catheters must be periodically flushed to ensure that there is not a build-up of particulates or residue in the lumen that could block or otherwise impede the flow of fluid out of the patient. In general, the flushing procedure typically involves attaching a source of flushing, or cleansing, fluid, such as a saline solution, and directing the cleansing fluid under low pressure through the tube or catheter to remove any buildup occurring in the lumen. The fluid is then allowed to flow out the tube or catheter into a drainage bag.

When it is desired to flush the tube or catheter, the drainage bag must be disconnected and the source of cleansing fluid, usually a syringe, is attached to the tube or catheter that is fluidly connected to the patient. Once the cleansing fluid has been directed into the tube or catheter, the syringe or other source of cleansing fluid, must be disconnected and the drainage bag reattached. This procedure is particularly unsatisfactory because of the time required to unscrew the drainage bag, attach the syringe, and then to unscrew the syringe and reattach the drainage bag. In addition, after the cleansing fluid has been directed into the tube or catheter that is attached to the patient, there is an enhanced risk of fluid leakage during the detachment and reattachment process. Such leakage can cause an unsanitary condition and may potentially expose medical personnel and the patient to contamination. Further, if any fluid is accidentally discharged during this process, the medical personnel must take the time to sanitize the patient, the bedding, and themselves.

Another device, commonly referred to as a stopcock, can be used to make the flushing procedure somewhat easier for medical personnel and to reduce the risk of contamination and spillage. The stopcock is attached to the tube or catheter that is in fluid communication with the patient, and thereby connects the tube or catheter to the drainage bag. Typically, the stopcock includes a valve that must be manually operated so that the flow of fluid is directed either into a drainage bag or to an outside port for periodic catheter maintenance or flushing. This allows the fluid source, such as a syringe, to be attached to the outside port when it is time to flush the tube or catheter. Once the syringe is attached, the stopcock is manually adjusted so as to stop the flow of fluid to the drainage bag. This operation allows the cleansing fluid to be directed into the tube or catheter. Once all the cleaning fluid is in the tube or catheter, the stopcock is manually adjusted back to its original position, wherein fluid is allowed to flow into the drainage bag.

While the stopcock represents somewhat of an improvement over the manual flushing procedure, there have been various problems with the stopcock. For example, stopcocks have failed from usage or have had certain limitations to their use. One of the problems with using a stopcock is that the nurse or attendant must manually adjust the stopcock to cease the flow of fluid in the drainage catheter, and then open the access port to enable the flushing fluid to be directed into the lumen of the tube or catheter. Once the cleansing fluid has been directed into the tube or the catheter, the stopcock must again be manually adjusted to redirect the fluid flow into the drainage bag. These extra steps are time consuming and cumbersome.

There is also a possibility that the manual adjustments that are required may confuse the medical personnel so that the fluid flow out of the patient is misdirected. In addition, if for some reason, the medical personnel fail to return the stopcock to the original position, so as to allow the fluid to flow to the drainage bag, fluid will flow out the access port and contaminate the patient as well as the surrounding area. In addition to creating a biohazard, such a situation could result in loss of fluids that are needed to monitor the health of the patient.

A further problem with existing stopcocks is that the diameter of the passageway formed through the stopcock is typically smaller the diameter of the lumen in the tube or catheter to which the stopcock is attached. As a result, the passageway of the stopcock impedes the fluid flow by creating a bottlenecking effect as the fluid tries to flow through the stopcock.

BRIEF SUMMARY OF EMBODIMENTS OF THE INVENTION

The present invention has been developed in response to the current state of the art, and in particular, in response to these, and other, problems and needs that have not been fully or adequately resolved by currently available valve apparatuses. Briefly summarized, embodiments of the present invention provide an improved valve apparatus which permits flushing of a drainage tube or catheter without necessitating the disconnection of the drainage tube or catheter from the patient or from the drainage bag, and which is suitable for use in conjunction with various medical instruments such as are typically employed to perform diagnostic, analytic, therapeutic, and other procedures.

Embodiments of the present invention are well suited for use in the context of the flushing of catheters, drainage tubes, and the like. However, it will be appreciated that embodiments of the present invention are suitable for use in any application or environment where it is desired to drain materials from a fluid source, aspirate material from a desired location, and/or introduce various materials to a desired location, in a simple and effective manner.

In one embodiment of the present invention, a valve apparatus is provided that includes a housing having proximal end, which includes a barb configured to mate with various standard catheters and drainage tubes, and a distal end. The housing further defines a passageway therethrough, and includes an access port defining a bore arranged for fluid communication with the passageway. A plunger, preferably comprising nylon or the like and having a bulb on the bottom and defining a flushing passage aligned with the bore, is slidingly disposed in the bore for reciprocal motion between an open and closed position, and at least partially resides within a sealing ring, having a plurality of wiper rings in contact with the plunger, also disposed in the bore. Both the plunger and sealing ring are securely retained within the bore by way of a first fitting, configured to mate with various standard medical devices such as syringes and the like, which defines a passageway in fluid communication with the bore and which engages corresponding retention tabs located on the housing. The first fitting further includes a shoulder so as to limit the upward range of motion of the plunger, slidingly received within the passageway defined by the fitting.

Disposed within the housing at its distal end is a hollow insert, preferably comprising a resilient material such as silicone or the like, and arranged so that a least a portion of the insert is disposed beneath the bore defined by the access port. The insert includes a flange that resides in a seat defined by the housing. Finally, a second fitting, preferably identical to the first fitting, is configured to be received within the insert and defines a passageway in communication therewith. The second fitting additionally includes a seat which contacts the flange of the insert when the second fitting is attached to the distal end of the housing.

During assembly, the sealing ring is disposed in the bore so that it contacts the seat defined within the bore. The plunger is then inserted into the bore and at least partially received by the sealing ring. The first fitting is attached to the access port and serves to compress the sealing ring onto the seat defined by the bore so as to substantially prevent leakage past the plunger. The insert disposed beneath the bore serves, by virtue of its resilience, to bias the plunger into an "open" position wherein the lower end of the flushing passage defined by the plunger is not aligned with the proximal end of the passageway of the housing, and wherein fluid is free to flow between the distal and proximal ends of the passageway. At the distal end of the housing, attachment of the second fitting causes the seat of the second fitting to contact and compress the flange of the insert, so as to substantially preclude leakage past the sides of the insert.

In operation, a syringe or other medical device attached to the first fitting acts to push the plunger down to the "closed" position wherein the lower end of the flushing passage is aligned with the proximal end of the passageway defined by the housing so that fluids introduced by the medical device may pass freely through the flushing passage and out of the valve apparatus by way of the proximal end of the passageway. Also, when the plunger is moved to the "closed" position by the medical device, the bulb on the bottom of the plunger serves to compress the portion of the insert disposed beneath the bore and thereby acts to substantially prevent fluid flow between the proximal and distal ends of the passageway. Upon removal of the medical device, the insert serves to bias the plunger back up into the "open" position.

In one embodiment of the invention, a medical instrument, such as an endoscopic device or guide wire, is disposed within the passageway and passes through the passageway and the catheter to which the valve apparatus is connected, and into the patient. Because the insert is resilient, it seals the passageway around the instrument during the flushing procedure. Accordingly, there is no need to remove the instrument in order to implement flushing of the catheter.

Embodiments of the present invention are thus effective in, among other things, permitting catheter flushing procedures to be performed without necessitating the disconnection of any of the elements of the catheter flushing and drainage system. Further, embodiments of the present invention are well suited for use in conjunction with various other medical procedures involving the use of instruments such as endoscopic devices, guide wires, and the like.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 9 is a cross section view of an embodiment of the sealing ring;

FIG. 10 is a cross section view of an embodiment of the plunger;

DETAILED DESCRIPTION OF VARIOUS EMBODIMENTS

Reference will now be made to figures wherein like structures will be provided with like reference designations. It is to be understood that the drawings are diagrammatic and schematic representations of various embodiments of the claimed invention, and are not to be construed as limiting the present claimed invention, nor are the drawings necessarily drawn to scale.

Figure 1:
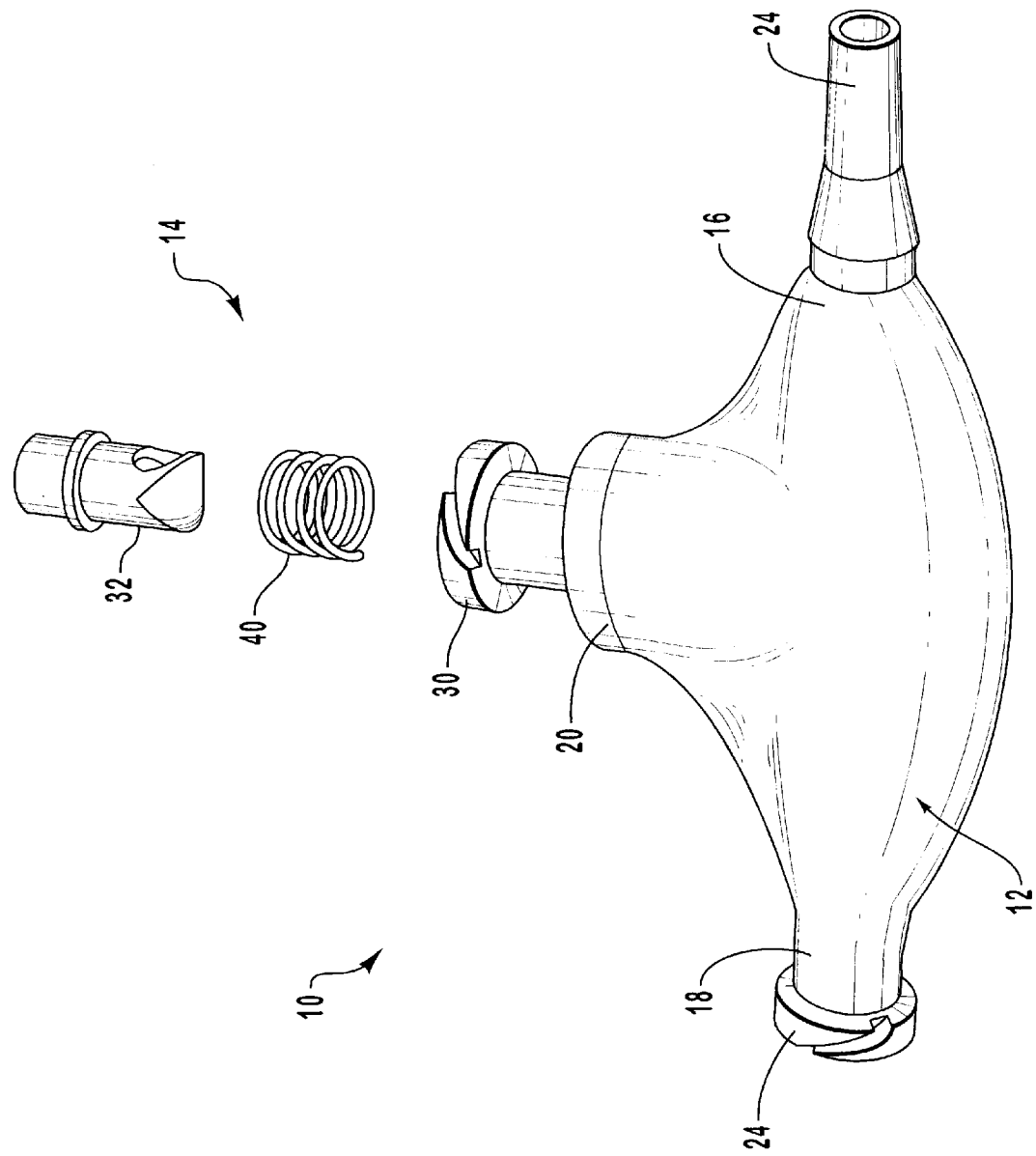
FIG. 1 is a partially exploded perspective view of one embodiment of a valve apparatus.
Figure 2:
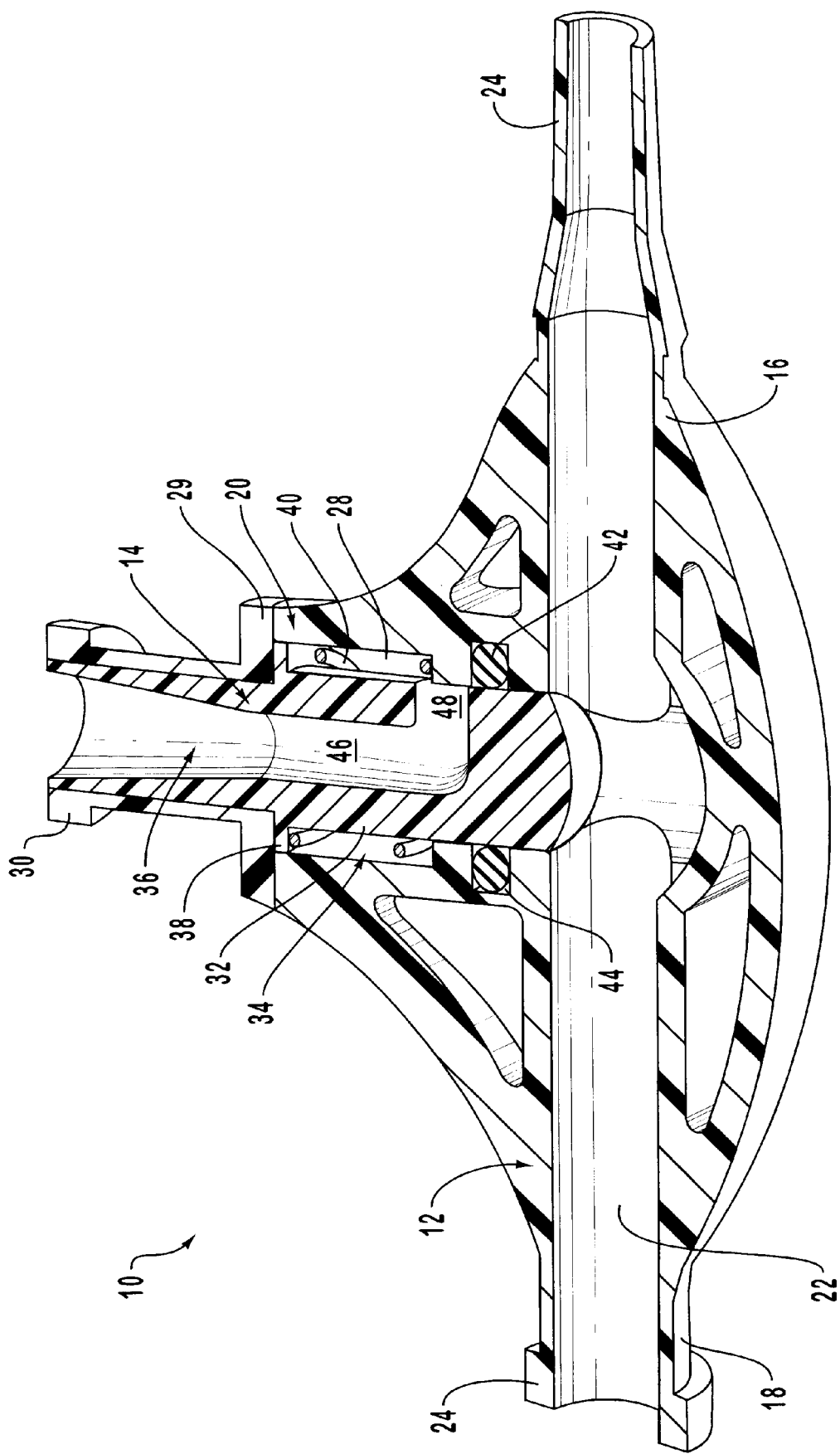
FIG. 2 is an enlarged cross-sectional view of the structure of FIG. 1 with the seal assembly in the open position.

Directing attention now to FIG. 1, an embodiment of a valve apparatus is indicated generally at 10. As illustrated, valve apparatus 10 comprises a housing 12 and a seal assembly 14. Housing 12 has a proximal end 16, a distal end 18, and an access port 20. As shown in FIG. 2, housing 12 has a passageway 22 that extends longitudinally therethrough. As a consequence of defining passageway 22, housing 12 likewise defines a proximal end of passageway 22 corresponding to proximal end 16 of housing 22, and a distal end of passageway 22 corresponding to distal end 18 of housing 12, as indicated in FIG. 2.

In one embodiment, passageway 22 is sized and configured to eliminate the typical bottlenecking-effect on fluid flow that is found in conventional stopcocks. As a result, the diameter of passageway 22 is larger than the diameter of a passageway found in a conventional stopcock. Various sizes and configurations of passageway 22, however, may be utilized in housing 12. Although the interior surface of passageway 22 is shown in FIG. 2 as being substantially smooth, it will be appreciated by one skilled in the art that in an alternate embodiment passageway 22 can be grooved.

As illustrated in FIGS. 1 and 2, proximal end 16 and distal end 18 of housing 12 each have a connector 24 attached thereto. While various types of connectors 24 may be utilized, FIGS. 1 and 2 depict connector 24 that is attached to proximal end 16 of housing 12 as being, by way of example and not limitation, a male Luer lock hub to allow connection with standard tubes and catheters. Correspondingly, distal end 18 of housing 12 may be equipped with connector 24 that in this case is in the form of a female Luer lock hub to allow housing 12 to be connected to various types of medical devices including tubes, catheters, and a drainage bag (not shown). It will be appreciated that the position of the male and female Luer lock hubs could be reversed or that both connectors 24 could be the same configuration without affecting the function thereof. Another type of connector that may be used is a pressure-fit connector. It will be appreciated that a combination of different types of connectors may also be used.

Housing 12 also includes access port 20. Access port 20 is used for maintenance procedures for the tube or catheter, such as a flushing process where fluids are introduced into the tube or catheter to remove any particulates or other materials which may build up on the interior surface of the lumen thereof. As illustrated in FIG. 2, access port 20 has a bore (not shown) formed therethrough that is selectively in fluid communication with passageway 22 of housing 12. The bore formed through access port 20 is substantially concentric to access port 20. It will be appreciated that this is not required. In addition, as shown in FIG. 2, the bore of access port 20 has a recessed chamber 28 formed therein that communicates with the bore formed in access port 20. In one embodiment, chamber 28 is concentric with the bore in access port 20. It can be appreciated that housing 12 may have various other configurations in order to carry out the intended function thereof.

The remote end of access port 20 is configured to be placed in fluid communication with a medical device. As depicted in FIGS. 1 and 2, the remote end of access port 20 includes a cap 29 with a connector 30 attached thereto for fluid coupling between a medical device (not shown) and access port 20. Cap 29 covers the remote end of access port 20. Cap 29 is attached to access port 20 of housing 12 using conventional attachment techniques including adhesives or welding. In one embodiment, connector 30 is a conventional female Luer lock hub. Like connectors 24, which were previously discussed, connector 30 could have various other configurations and be a different type of connector other than a Luer lock hub. In addition, connectors 24 and 30 may have threads formed thereon to accommodate a conventional Luer lock attachment. Various other types of attachment structure or connectors may perform the attaching function of connectors 24 and 30.

The exterior of housing 12 is depicted in FIG. 1 as being substantially smooth. It will be appreciated that, the exterior of house 12 could have other configurations without affecting the function thereof. Although housing 12 is depicted as having one access port 20, housing 12 could have more than one access port attached thereto. In addition, in FIG. 2, access port 20 of housing 12 is depicted as being at an angle to passageway 22 formed through housing 12. It is contemplated that access port 20 could be positioned at various other angles relative to the longitudinal axis of passageway 22 than that illustrated in the figures. The angle of access port 20 is not important as long as access port 20 is in communication with passageway 22 formed through housing 12. It is intended that various other configurations of access port 20 are capable of performing the function thereof with equal effectiveness.

Figure 3:
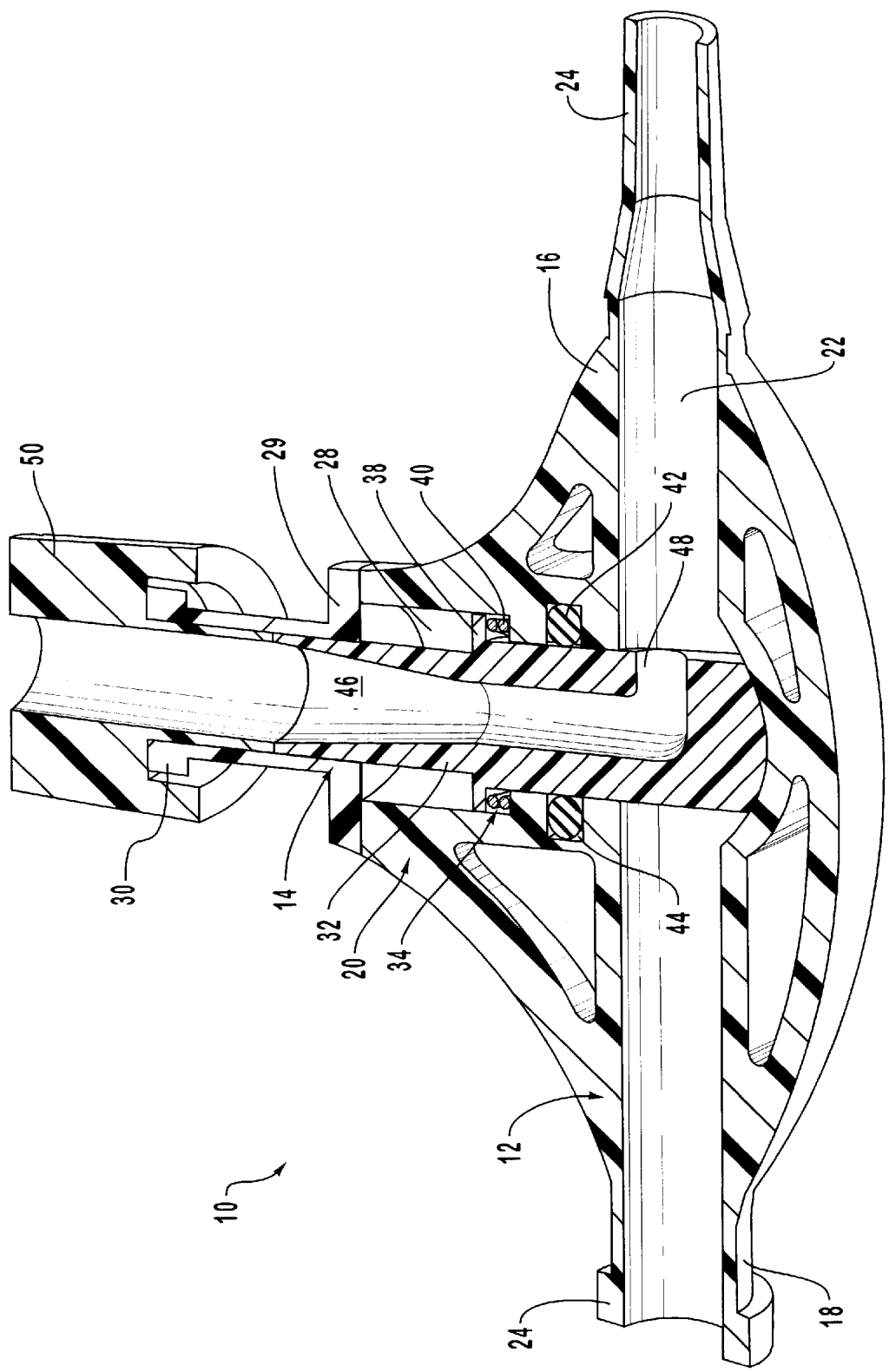
FIG. 3 is an enlarged cross-sectional view of the structure of FIG. 1 with the seal assembly in the closed position.

Valve apparatus 10 also includes seal assembly 14. Seal assembly 14 is configured to cooperate with the bore (not shown) formed in access port 20 and passageway 22. Seal assembly 14 automatically seals and unseals passageway 22 in housing 12 in response to a medical device being attached to connector 30 on the remote end of access port 20. Seal assembly 14 has an open position in which passageway 22 of housing 12 is capable of having fluid flow therethrough (FIG. 2) and a closed position in which the fluid flow through passageway 22 is interrupted and passageway 22 is sealed to prevent fluid from flowing out passageway 22 (FIG. 3). Seal assembly 14 automatically moves between the open position and the closed position in response to a medical device being mounted on connector 30 of access port 20. Seal assembly 14 is biased into the normally open position illustrated in FIG. 2.

Referring to FIG. 2, seal assembly 14 comprises a seal 32 and a biasing mechanism 34. Seal 32 is configured to cooperate with the bore and chamber 28 formed in access port 20 of housing 12 and is movably disposed in access port 20 for reciprocal motion between the open and closed positions, as indicated collectively by FIGS. 2 and 3. Seal 32 has a flushing passage 36 formed therethrough. The exterior surface of seal 32 is configured to cooperate with the inner surface of the bore in access port 20. In one embodiment, seal 32 has a generally cylindrical shape and comprises a collar 38 that extends substantially outward from the exterior surface of seal 32. Collar 38 of seal 32 has an outer diameter approximately equal to the diameter formed by the inner surface of chamber 28. It can be appreciated that seal 32 may have other configurations as long as seal 32, the bore of access port 20, and chamber 32 are configured to cooperate and to allow seal 32 to be movably disposed in the bore of access port 20. The end of seal 32 proximate to passageway 22 is configured to sealingly engage the interior surface of passageway 22 when seal assembly 14 is in the closed position depicted in FIG. 3.

As previously discussed, seal 32 is biased into the normally open position depicted in FIG. 2. Seal 32 is configured to automatically move between the open and closed position thereby sealing and unsealing passageway 22 in response to a medical device being attached to access port 20. Seal 32 has a normally open position depicted in FIG. 2 in which passageway 22 is open and a closed position shown in FIG. 3 in which passageway 22 is sealed. Seal 32 may be composed of a resilient material such as a rubber or various other polymer materials.

Seal assembly 14 also comprises biasing mechanism 34 that is configured to urge seal 32 into the normally open position. In one embodiment, biasing mechanism 34 comprises a resilient flexible member 40, such as a spring, and collar 38 attached to seal 32. Spring 40 and collar 38 are disposed in chamber 28 of access port 20. Spring 40 is sized and configured so as to cooperate with collar 38 of seal 32 while being disposed in chamber 28. Spring 40 urges collar 38 and, consequently, seal 32 toward the remote end of access port 20. As a result, biasing mechanism 34 urges seal 32 into the normally open position. Resilient flexible member 40 may have various other configurations known by those skilled in the art such as a leaf spring or a resilient polymer seal.

In addition, it will be appreciated that biasing mechanism 34 may be located in various other positions and perform the function thereof. By way of example, instead of being disposed in chamber 28 of access port 20, biasing mechanism 34 could be attached to the exterior of access port 20. In that case connector 30 would be a male Luer lock assembly. Biasing mechanism would be attached to seal 32 through openings or slots formed in the wall of access port 20. Alternatively, collar 38 of seal 32 would extend outside of access port 20. In these embodiments, biasing mechanism 34 would comprise a resilient material that allows seal to move between a closed position and an open position but urges seal assembly 14 to return to the open position.

Biasing mechanism 34 is one embodiment of structure capable of performing the function of a biasing means for urging seal 32 into the open position. It can be appreciated various other embodiments of structure are capable of performing the function of such a biasing means for urging seal 32 into a normally open position. In addition, other structures capable of performing the function of a biasing means include, by way of example and not limitation, various other resilient members positioned within the bore of access port 20 to create resistance against seal 32.

Valve apparatus 10 also comprises a secondary seal 42. In one embodiment, secondary seal 42 is an O-ring that is disposed in an annular groove 44 formed in the bore of access port 20 proximate to passageway 22. Secondary seal 42 prevents any fluid from seeping around the exterior surface of seal 32. Other embodiments of secondary seal 42 to prevent fluid seepage around the exterior surface of seal 32 are known by those skilled in the art. Further, instead of having secondary seal 42 distinct from seal 32, secondary seal 42 could be attached to seal 32 toward the end thereof proximate to passageway 22. This would eliminate the need for annular groove 44 as long as chamber 28 was configured to cooperate with the outside diameter of secondary seal 42.

FIG. 3 depicts seal 32 in the closed position upon a medical device 50 being attached to connector 30 of access port 20. Attaching medical device 50 to connector 30 causes the connector on medical device 50 to act on seal assembly 14 as will be discussed below in further detail. When seal 32 is in the closed position, flushing passage 36 in seal 32 communicates with the bore in access port 20 and provides an opening to passageway 22. Upon seal 32 moving to the closed position, fluid having a slight pressure can be directed into flushing passage 36 and enters passageway 22 thereby flushing the tube or catheter and cleaning out any particulates or blockages which may have formed therein. As soon as the cleansing fluid has been directed into the tube or catheter, medical device 50, such as a syringe, is unhooked from connector 30 on access port 20, and seal 32 automatically returns to the open position illustrated in FIG. 2 due to biasing mechanism 34 urging seal 32 toward the remote end of access port 20. As a result, passageway 22 goes from being in the closed position, as shown in FIG. 3, to being in the normally open position shown in FIG. 2.

As illustrated in FIGS. 2 and 3, in one embodiment flushing passage 36 formed through seal 32 has a first end 46 and a second end 48. First end 46 of flushing passage 36 is substantially parallel to the longitudinal axis of seal 32. In contrast, second end 48 of flushing passage 36 is substantially parallel to the longitudinal axis of passageway 22 of housing 12. As depicted, first end 46 and second end 48 of flushing passage 36 are substantially perpendicular thereby forming a right angled turn. It can be appreciated by those skilled in the art that flushing passage 36 of seal 32 may have various other configurations. For example, first end 46 and second end 48 of flushing passage 36 could have a more gradual curvature. The specific configuration of flushing passage 36 is not particularly important as long as fluid that is directed through access port 20 enters flushing passage 36 of seal 32 in access port 20 and exits seal 32 into passageway 22 of housing 12 so that the tube or catheter can be flushed. By way of example and not limitation, it can be appreciated that seal assembly 14 is one embodiment of structure capable of performing the function of sealing means for selectively sealing and unsealing passageway 22 of housing 12.

The inventive design of valve assembly 10 provides sterile access to, for example, a drainage catheter previously placed in the patient to remove obstructed bile, urine, or pus. Valve apparatus 10 allows a physician, patient, or nurse to use a standard Luer lock syringe to sterilely flush the catheter or tube. Further, unlike existing flush systems, valve apparatus 10 removes any possibility that a person flushing the catheter or tube will accidentally leave valve apparatus 10 in the closed position causing fluid to be misdirected. Rather than having medical personnel struggle to know which way the stopcock arm should be turned to direct flow, valve apparatus 10 with seal assembly 14 automatically moves between the open positing and the closed position in response to a medical device 50, such as a syringe, being attached to access port 20.

One method of using valve apparatus 10 is by actuating seal assembly 14 using the manual compression caused by attaching a medical device 50 to the remote end of access port 20 as depicted in FIG. 3. The force exerted on seal assembly 14 by attaching syringe 50 to connector 30 on remote end of access port 20 overcomes the resistance force exerted on seal assembly 14 by biasing mechanism 34. Specifically, when syringe 50 is either Luer or friction locked into the remote end of access port 20, the forces acting on seal 32 by the connector of syringe 50 overcomes the biasing forces of spring 40 and automatically moves seal 32 to the closed position.

Once seal 32 has been moved to the closed position and passageway 22 is sealed, a one-way flush stream of cleansing fluid is directed into the tube or catheter from syringe 50 to clear the tube or catheter of any debris or build-up that might be in the lumen thereof. Upon syringe 50 being removed from connector 30 on access port 20, spring 40 urges seal 32 toward the remote end of access port 20. Consequently, seal 32 automatically moves back to the normally open position and allows the tube or catheter to drain by gravity. It can be appreciated that various other connectors and methods can be used to overcome the resistance of spring 40 to move seal 32 to the closed position.

Figure 4:
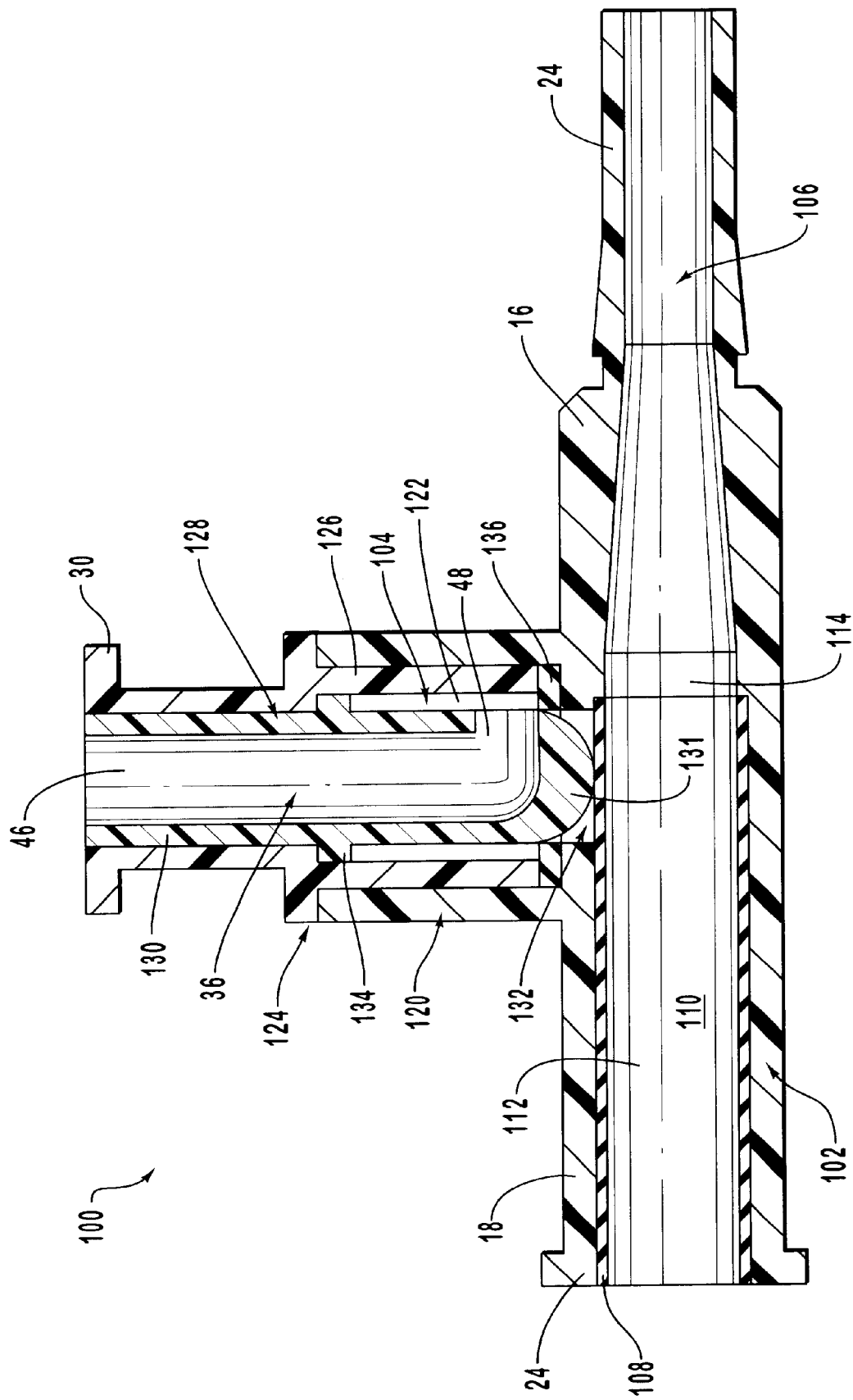
FIG. 4 is an enlarged cross-sectional view of another embodiment of a valve apparatus with a seal assembly in the open position.
Figure 5:
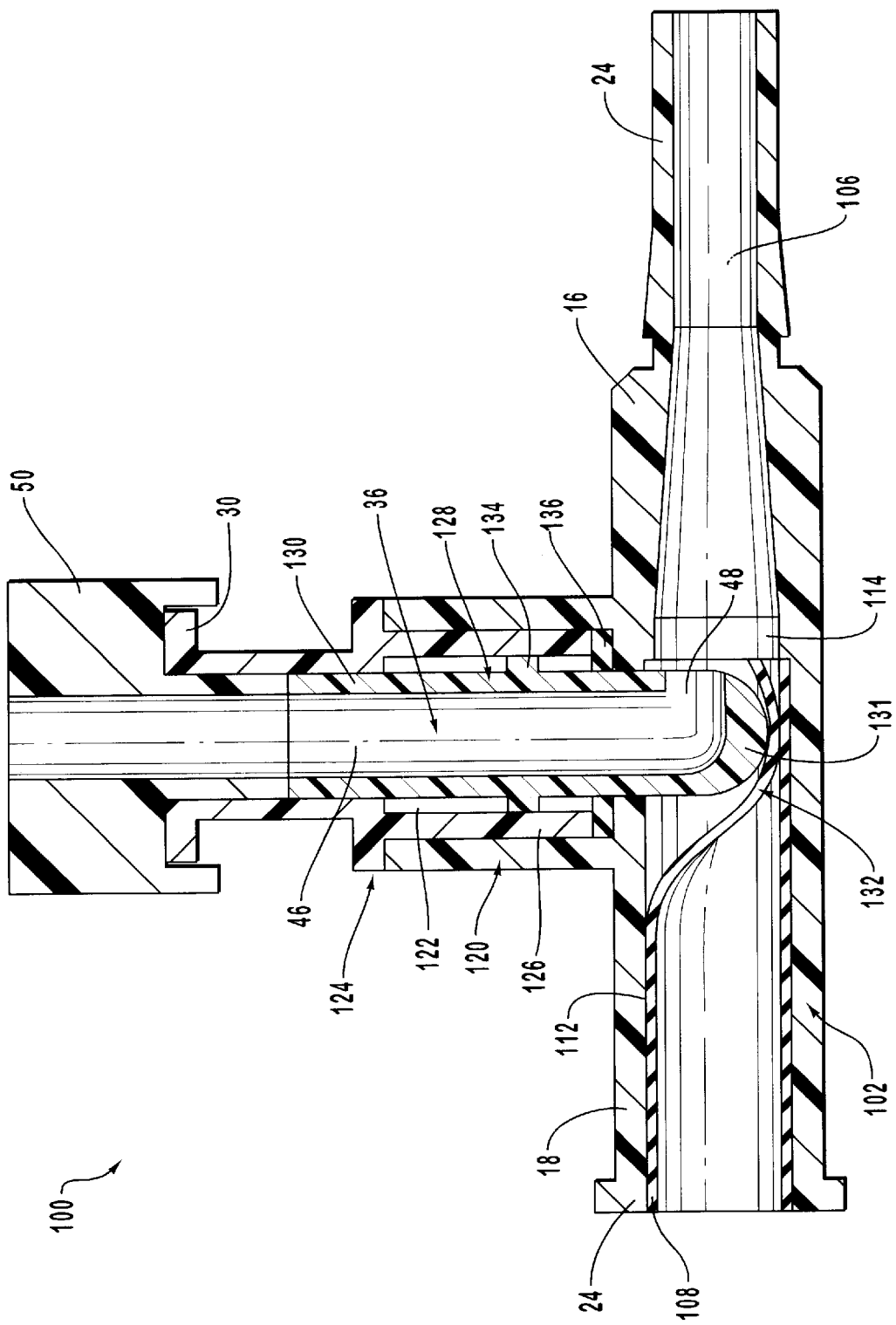
FIG. 5 is an enlarged cross-sectional view of the structure of FIG. 4 with the seal assembly in the closed position.

FIGS. 4 and 5 illustrate a second embodiment of a valve apparatus, indicated generally at 100. The majority of the features previously discussed apply to valve apparatus 100. The features that are not affected are identified with the same reference numbers as used in FIGS. 1 through 3. Only those features that have changed will be described in detail.

As illustrated in FIG. 4, valve apparatus 100 comprises a housing 102 and seal assembly 104. Housing 102 has a passageway 106 that extends longitudinally therethrough. The interior surface of passageway 106 has been sized and configured to receive a resilient flexible member 108 therein. In one embodiment, resilient flexible member 108 comprises tubing.

Passageway 106 includes a first portion 112 and a second portion 114 proximate to resilient flexible member 108. The diameter of first portion 112 is larger than the diameter of second portion 114. As a result, the interior surface of passageway 106 has a step formed therein to receive the end of resilient member 108. It can be appreciated that the interior surface of passageway 102 could have various other configurations as long as it is configured to cooperate with the end of resilient member 108. Resilient member 108 has a lumen 110 formed therethrough with a diameter that is substantially the same as the diameter of second portion 114 of passageway 106. This allows passageway 106 and the inside surface of lumen 110 to form a substantially continuous and smooth surface.

Housing 102 also includes an access port 120 that has a bore (not shown) formed therethrough that is selectively in fluid communication with passageway 106 of housing 102. In one embodiment of valve apparatus 100, access port 120 is substantially perpendicular to passageway 106 formed through housing 102. It will be appreciated that access port 120 could have various other orientations relative to passageway 106 in housing 102. As illustrated in FIG. 4, the bore of access port 120 also has a recessed chamber 122 formed therein that is concentric with the bore formed in access port 120. The bore formed through access port 120 is substantially concentric to access port 120. It will be appreciated that various other configurations and orientations of the bore through access port 120 could be used without affecting the function thereof.

Access port 120 includes a cap 124 attached to the remote end thereof. Cap 124 comprises a connector 30 that extends outwardly from access port 120 and a downwardly extending leg 126. The exterior surface of downwardly extending leg 126 is sized and configured to cooperate with the inside surface of chamber 122. Cap 124 is attached to access port 120 of housing 102 using conventional attachment techniques including, but not limited to, adhesives or welding.

Valve apparatus 100 also includes a seal assembly 128 that is depicted in FIG. 4. Seal assembly 128 is configured to cooperate with the bore (not shown) formed in access port 120 and to automatically seal and unseal passageway 106 in housing 102 in response to a medical device 50 being attached to connector 30. Seal assembly 128 has an open position in which the passageway of housing 102 is capable of having fluid flow therethrough (FIG. 4) and a closed position in which the fluid flow through passageway 106 is interrupted and passageway 106 is sealed to prevent fluid flow from flowing to the drainage bag (FIG. 5). Seal assembly 128 is biased into a normally open position illustrated in FIG. 4 as will be discussed in further detail below.

Referring to FIG. 4, seal assembly 128 comprises a seal 130 and a biasing mechanism 132. Seal 130 is configured to cooperate with bore and chamber 122 formed in access port 120 of housing 102 and is movably disposed in access port 120. Like seal 32 shown in FIGS. 2 and 3, seal 130 has a flushing passage 36 formed therethrough and is configured to cooperate with the inner surface of the bore in access port 120.

In one embodiment, seal 130 includes an optional collar 134 that extends outward from the exterior surface of seal 130. Collar 134 of seal 130 has an outer diameter approximately equal to the diameter of formed by the inside diameter of leg 120. It will be appreciated that seal 130 may have other configurations as long as seal 130, the bore and chamber 122 of access port 120, and leg 120 of cap 124 are configured to cooperate so that seal 130 is movably disposed in the bore of access port 120. For example, if collar 134 was eliminated, the outside surface of seal 130 would contact the inside diameter of leg 120 of cap 124.

As previously discussed, seal 130 is biased into the normally open position depicted in FIG. 4. Seal 130 is configured to move automatically between the open and closed position thereby sealing and unsealing passageway 106 in response to medical device 50 being attached to access port 120. Seal 130 has the normally open position depicted in FIG. 4 in which passageway 106 is open and a closed position shown in FIG. 5 in which the passageway is sealed.

Seal assembly 128 also comprises a biasing mechanism 132 that is configured to urge seal 130 into the normally open position. In one embodiment, biasing mechanism 132 comprises resilient flexible member 108 and proximate end 131 of seal 130. It can be appreciated that various other types of biasing mechanisms 132 can be used to perform the function thereof as will be discussed in further detail. Proximate end 131 of seal 130 is configured to engage the exterior surface of resilient flexible member 108 disposed in passageway 106 of housing 102 when seal assembly is in the closed position depicted in FIG. 5. As previously discussed, in one embodiment, resilient flexible member 108, illustrated in FIG. 4, comprises tubing disposed in passageway 106. When seal assembly 128 moves to the closed position depicted in FIG. 5, proximate end 131 of seal 130 engages the outside diameter of tubing 108 causing the end of tubing 108 to pinch down on itself, thereby sealing lumen 110 in tubing 108 and, as a result, passageway 106 though housing 102. Tubing 108 can be comprised of various materials including, but not limited to, rubber, silicon, or other resilient materials. Tubing 108 must, however, be sufficiently flexible to form a seal when seal 130 is in the closed position and resilient enough to exert biasing forces on seal assembly 128.

When medical device 50 is removed from connector 30 on an access port 120, tubing 108 exerts a biasing force on proximate end 131 of seal 130 sufficient to urge seal 130 toward connector 30 and to return seal 130 to the normally open position. It will be appreciated that resilient flexible member or tubing 108 may have other configurations known by those skilled in the art. Tubing 108 is one embodiment of structure capable of performing the function of a biasing means for urging seal 130 into the open position. It can be appreciated that various other embodiments of structure are capable of performing the function of such a biasing means for urging seal into a normally open position. Other structures capable of performing the function of a biasing means include, by way of example and not limitation, various other resilient members positioned within passageway 106 of housing 102 capable of forming a seal against itself when seal 130 is in the closed position and resilient enough to urge seal 130 toward connector 30 and to return to the open position.

Valve apparatus 100 also comprises a secondary seal 136. In one embodiment, secondary seal 136 comprises a washer that is disposed in chamber 122 of access port 120. Other embodiments of secondary seal 136 to prevent fluid seepage around the exterior surface of seal are known by those skilled in the art. In addition, although secondary seal 136 is illustrated as being positioned in access port 120 near proximate end 131 of seal 130, it will be appreciated that secondary seal 136 may have various other positions within seal assembly 128. In addition, secondary seal 136 may have various other shapes and configurations than that depicted in FIGS. 4 and 5. By way of example and not limitation, secondary seal 136 may be attached to seal 132. The specific location of secondary seal is not particularly important. What is important, is that secondary seal 136 prevents fluid leakage from passageway 106 in housing 102.

The ability for valve apparatus 10 and 100 to automatically move between an open and a closed position provides a solution for several drainage complications. Seal assemblies 14 and 128 automatically move between sealing and unsealing passageway 22 and 106 within housing 12 and 102, respectively, without having to disconnect the catheter tubing or worry about directing flow by manually switching a valve on a conventional stopcock. Valve apparatus 10 and 100 are a no-nonsense, user-friendly, automatic device that will not restrict the fluid flow of tube or catheter.

It is envisioned that valve apparatus 10 and 100 will be used in a variety of applications involving tubes or catheters. In particular, one application is using valve apparatus 10 or 100 following the percutaneous or surgical placement of drainage catheters or tubes into obstructed organs, such as the urinary tract, or the biliary track to allow drainage of potentially infective body fluids such as urine or bile. Valve apparatus 10 or 100 may also be used with catheters or tubes that have been placed into abscess cavities. Valve apparatus 10 or 100 will be inserted within the drainage system between the catheter which has been placed within a body cavity and a drainage receptacle such as an enclosed drainage bag. Typically valve apparatus 10 or 100 will be actuated by flushing the system three to four times daily to prevent the accumulation of debris in the drainage catheter. It is contemplated that valve apparatus 10 or 100 may have utility for angiography applications or other applications within the cardiovascular or intravenous system. It is further envisioned that more than one valve apparatus 10 or 100 may be used in a series.

Figure 6:
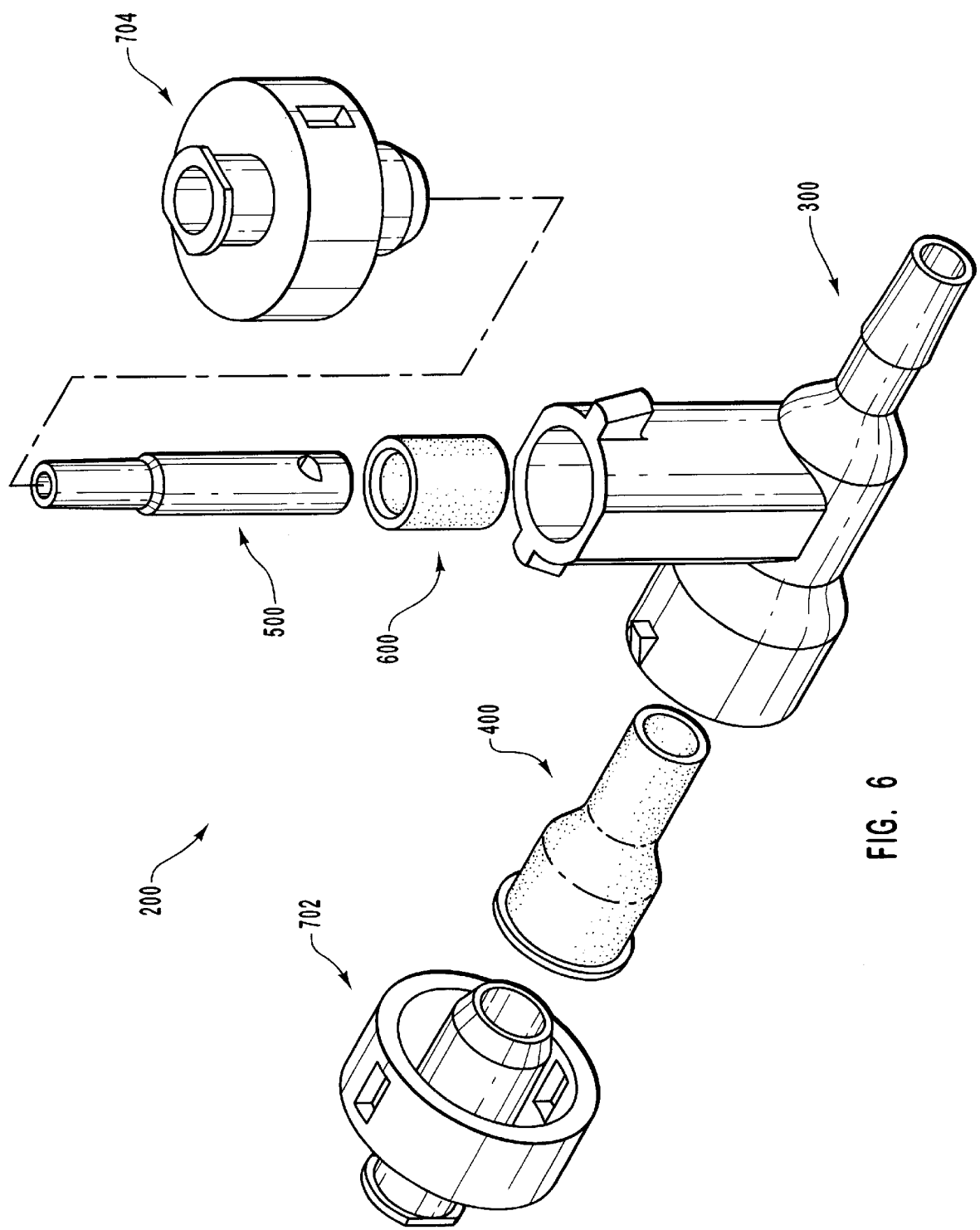
FIG. 6 is an exploded perspective view of another embodiment of a valve apparatus.

Directing attention now to FIGS. 6 through 14, an alternative embodiment of the valve apparatus is indicated generally at 200. With particular reference to FIG. 6, valve apparatus 200 includes a housing 300 configured to receive therein an insert 400. Further, valve apparatus includes a plunger 500 disposed within housing 300 and slidingly received by sealing ring 600. Finally, two fittings, 702 and 704, serve to secure insert 400, and plunger 500 and sealing ring 600, respectively, within housing 300. As discussed below, valve apparatus is effective in, among other things, facilitating drainage of fluid from a fluid source, such as the body of a patient, and may also be used to aspirate materials from a fluid source, and/or to flush various medical devices. Note that, as contemplated herein, "fluid" includes, but is not limited to, gases, liquids, gas-liquid combinations, as well as gases or liquids having entrained solid matter.

Figure 7:
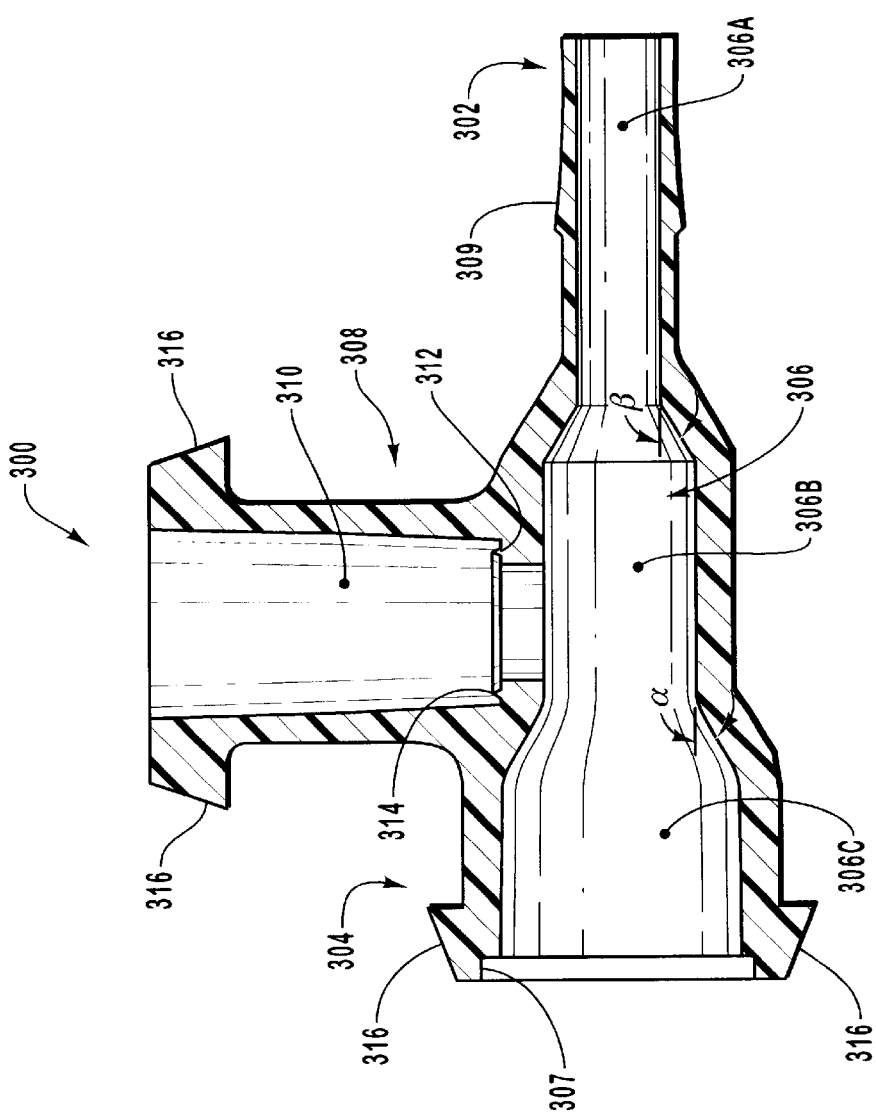
FIG. 7 is a cross section view of an embodiment of the housing.

Directing attention now to FIG. 7, and with continuing attention to FIG. 6, additional details are provided regarding various features of an embodiment of housing 300. Generally, housing 300 is substantially composed of a chemically inert translucent plastic, preferably polycarbonate or the like, and is molded or formed as a single piece. It will be appreciated however, that various other materials may be substituted for polycarbonate without impairing in any way the functionality provided by embodiments of the present invention. In general, any material(s) or combination thereof which provides the functionality of polycarbonate is contemplated as being within the scope of the present invention.

Housing 300 includes a proximal end 302 and distal end 304, and defines a passageway 306 which extends from proximal end 302 to distal end 304. Preferably, passageway 306 comprises three general segments, or portions, a proximal portion 306A, a central portion 306B, and a distal portion 306C which terminates in an annular ring 307 adapted to receive a flange of insert 400 (discussed below). Preferably, proximal portion 306A is defined by housing 300 to have a diameter somewhat smaller than the diameter of central portion 306B, so that a transition angle α, preferably about 30°, is cooperatively defined by proximal portion 306A and central portion 306B of passageway 306. In similar fashion, the diameter of central portion 306B is preferably somewhat smaller than the diameter of distal portion 306C of passageway 306, and a transition angle β, preferably about 30°, is cooperatively defined by central portion 306B and distal portion 306C, as indicated.

It will be appreciated that the aforementioned diametric relations and transition angles are exemplary, and that various other combinations of diameters and/or transition angles may be employed as required to suit a particular application and/or to facilitate achievement of one or more desired results with respect to the operation and functionality of embodiments of valve apparatus 200. Further, with respect to proximal end 302 of housing 300, it will be appreciated that various physical configurations may be employed as required to insure that the geometry of housing 300 comports with a desired international standard, such as for the attachment of drainage tubes, catheters or the like. By way of example, one embodiment of the present invention includes one or more barbs 309 disposed about proximal end 302 of housing 300 and adapted to retain a Luer locking ring on proximal end 302.

With continuing reference to FIG. 7, housing 300 further includes an access port 308, preferably having an exterior configuration substantially identical to that of proximal end 302 of housing 300, and defining a bore 310 configured and arranged for fluid communication with passageway 306. Such fluid communication is achieved by way of plunger 500 and sealing ring 600 (FIG. 6), discussed in further detail below. Defined within bore 310 is an annular shoulder 312 having disposed thereon a seat 314, preferably comprising a substantially triangular cross section. It will be appreciated that variables including, but not limited to, the size, number, geometry, and arrangement of seat(s) 314 may be varied as required to suit a particular application and/or to facilitate achievement of one or more desired results. Preferably, seat 314 is integral with annular shoulder 312.

Directing continued attention to housing 300, distal end 304 and access port 308 of housing 300 each include a plurality, preferably two, of respective integral retention tabs 316 configured to be permanently received in corresponding slots defined by fittings 702 and 704 (FIG. 11), so that insert 400, plunger 500, and sealing ring 600 are securely and permanently confined within housing 300 when fittings 702 and 704 are attached to housing 300. Note that while housing 300 preferably includes retention tabs 316 configured to mate with corresponding slots of fittings 702 and 704, it will be appreciated that housing 300 may include various other structure or devices suitable for joining housing 300, either permanently, or removably, to fittings 702 and 704. Alternatively, fittings 702 and 704 may be permanently attached to housing 300 by ultrasonic welding or similar processes.

Figure 8:
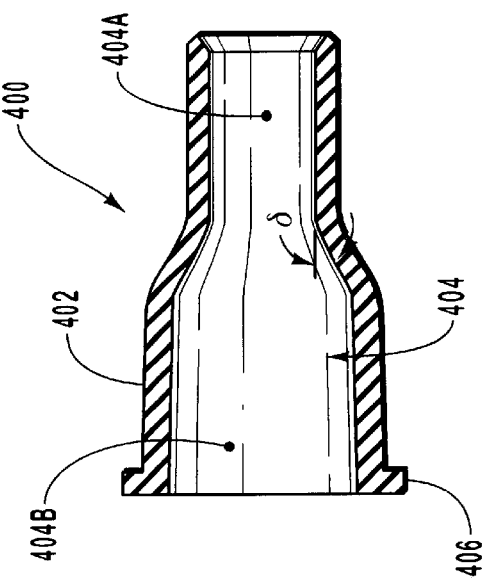
FIG. 8 is a cross section view of an embodiment of the insert.

Directing attention now to FIG. 8, and with continuing reference to FIGS. 6 and 7, various details are provided regarding features of an embodiment of insert 400. Generally, insert 400 is preferably composed of silicone or the like, and is configured so as to fit snugly within the space collectively defined by distal portion 306C and central portion 306B of passageway 306. Further, insert 400 includes a body 402 defining a passageway 404 which communicates with proximal portion 306A of passageway 306 when insert 400 is fully received in housing 300.

Note that while insert 400 is preferably composed of silicone or the like, any other material(s), or combinations thereof, providing the functionality of silicone, as disclosed herein, is contemplated as being within the scope of the present invention. Further, insert 400 may be formed by a variety of processes. Preferably, insert 400 comprises molded silicone tubing formed to the desired configuration.

As indicated in the illustrated embodiment, passageway 404 of insert 400 includes a proximal portion 404A and a distal portion 404B. Body 402 of insert 400 defines a transition angle δ between distal portion 404B and proximal portion 404A of passageway 404, preferably about 30°, that substantially comports with the corresponding geometry defined by transition angle α of housing 300. However, it will be appreciated that various other transition angles δ and/or α may be employed as required to suit a particular application and/or to facilitate achievement of one or more desired results. Preferably, transition angles δ and α are selected so as to minimize the likelihood of undesirable collection of fluid or other matter within housing 300, while also allowing efficient and uninterrupted flow through housing 300 with only minimal pressure drop. In particular, because the exterior geometry of insert 400 preferably substantially mirrors the geometry of passageway 306, pools and "dead" or stagnant flow spots within valve apparatus 200, where fluid or other materials would be likely to accumulate, are substantially eliminated. It will be appreciated this is a particularly useful feature in the context of medical applications of valve apparatus 200 where cleanliness and sanitation are often relevant.

With continuing attention to the geometry of insert 400, proximal portion 404A of passageway 404 is preferably slightly flared at the opening so as to readily admit materials flowing from proximal portion 306A to distal portion 306C of passageway 306 of housing 300. It will be appreciated however, that various other geometries may be desirable, depending upon variables such as the application in which valve apparatus 200 is to be used, and/or the operating conditions to which valve apparatus 200 will be subjected.

Finally, insert 400 includes an integral flange 406. When insert 400 is fully received within housing 300, integral flange 406 seats on and fits within annular ring 307 (FIG. 7) defined at distal end 304 of housing 300. At the same time, that portion of body 402 which defines proximal portion 404A of passageway 404 is disposed directly beneath bore 310 defined by access port 308 of housing 300. As suggested above, insert 400 is configured and arranged so that when it is received housing 300, a flow of fluid can readily pass between proximal portion 306A and distal portion 306C of passageway 306, by way of passageway 404 of insert 400. As discussed in further detail below in the context of fittings 702 and 704, passageway 404 defined by insert 400 is preferably characterized by a geometry that substantially comports with fitting 702.

Directing attention now to FIG. 9, and with continuing attention to FIGS. 6 and 7, additional details are provided regarding various features of an embodiment of plunger 500. Preferably, plunger 500 is substantially composed of a durable and chemically inert material such as nylon, Teflon, or the like. However, any other material or combination thereof suitable for use as described and disclosed herein is contemplated as being within the scope of the present invention. Plunger 500 includes a generally cylindrical body 502 which includes an annular shoulder 504, and which defines a flushing passage 506 having a substantially vertical run 506A in fluid communication with a substantially horizontal run 506B, and including a flushing passage inlet 506C, and two opposing flushing passage outlets 506D. The portion of cylindrical body 502 below shoulder 504 has a diameter substantially the same as inside diameter $D_2$ of sealing ring 600 (FIG. 10). In one embodiment of the present invention, plunger 500 includes a bulb 508, preferably integral with body 502. The size of bulb 508 may be varied as desired. In one embodiment, bulb 508 substantially encompasses the entire bottom of plunger 500.

Note that while flushing passage 506 is preferably configured to describe an inverted substantially "T"-shaped form, various aspects of flushing passage 506 may be adjusted as required. In particular, variables including, but not limited to, the size and geometry of flushing passage 506 may be varied either alone and/or in combination to facilitate achievement of one or more desired results and/or to suit a particular application. For example, in an alternative embodiment, flushing passage 506 is arranged substantially in the shape of an "L" so that only a single flushing passage outlet 506D is provided. As another example, flushing passage inlet 506C is preferably substantially circular in shape, and flushing passage outlets 506D preferably describe a semi-circular shape. However, it will be appreciated that various other geometries may alternatively be employed. In any event, vertical run 506A of flushing passage 506 is preferably configured and arranged for fluid communication with a medical device (FIG. 13) attached to a fitting 702 (FIG. 11A), and horizontal run 506B of flushing passage 506 is preferably configured and arranged for selective fluid communication with passageway 306.

Directing attention now to FIG. 10, and with continuing attention to FIGS. 6, 7 and 9, additional details are provided regarding various features of an embodiment of sealing ring 600. Generally, sealing ring 600 comprises a resilient and chemically inert material, preferably silicone or the like, and defines an outside diameter $D_1$ that is substantially the same as the diameter defined by bore 310 of access port 308, so that sealing ring 600 may be readily fitted within bore 310 during assembly of valve apparatus 200. Sealing ring 600 additionally includes an upper sealing surface 602, and a lower sealing surface 604 in substantial contact with seat 314 of housing 300 when sealing ring 600 is disposed in bore 310. As discussed in greater detail below in the context of fitting 704, upper sealing surface 602 is arranged to contact fitting 704 and form a seal therewith. At least upper sealing surface 602, and preferably lower sealing surface 604 as well, defines a lead-in angle θ, preferably about 30°, which serves to provide a relative increase in the area of upper sealing surface 602 and thereby contributes to an improved seal between fitting 704 and sealing ring 600.

In addition to outside diameter $D_1$, sealing ring 600 further defines an inside diameter $D_2$ that is slightly larger than the outside diameter of plunger 500, discussed below, so that plunger 500 may be slidingly received within sealing ring 600. Finally, sealing ring 600 includes a plurality of integral wiper rings 606, each preferably characterized by a substantially triangular cross section. However, it will be appreciated that wiper rings 606 of various other geometries may be usefully employed as well. As indicated in FIG. 10, wiper rings 606 describe a diameter $D_3$ somewhat smaller than inside diameter $D_2$ of sealing ring 600. Generally, wiper rings 606 serve to clean and seal the outside surface of plunger 500 when it is retracted from central portion 306B of passageway 306. Finally, it will be appreciated that variables including, but not limited to, the number, size, geometry, and arrangement of wiper rings 606 may be varied either alone or in combination as required to suit a particular application and/or to facilitate an achievement of one or more desired results.

As noted earlier, fittings 702 and 704 serve to securely retain insert 400, plunger 500, and sealing ring 600 within housing 300 of valve apparatus 200. Directing attention now to FIGS. 11A and 11B, and with continuing reference to FIGS. 6 and 7, various details are provided regarding features of embodiments of fittings 702 and 704. Preferably, fittings 702 and 704 are substantially identical. Nevertheless, as the respective functionalities of fittings 702 and 704 vary somewhat, it will be appreciated that fittings 702 and/or 704 may take any of a variety of forms consistent with their functionality. In view of the foregoing, each fitting will be described in turn.

Figures 11A, 11B:
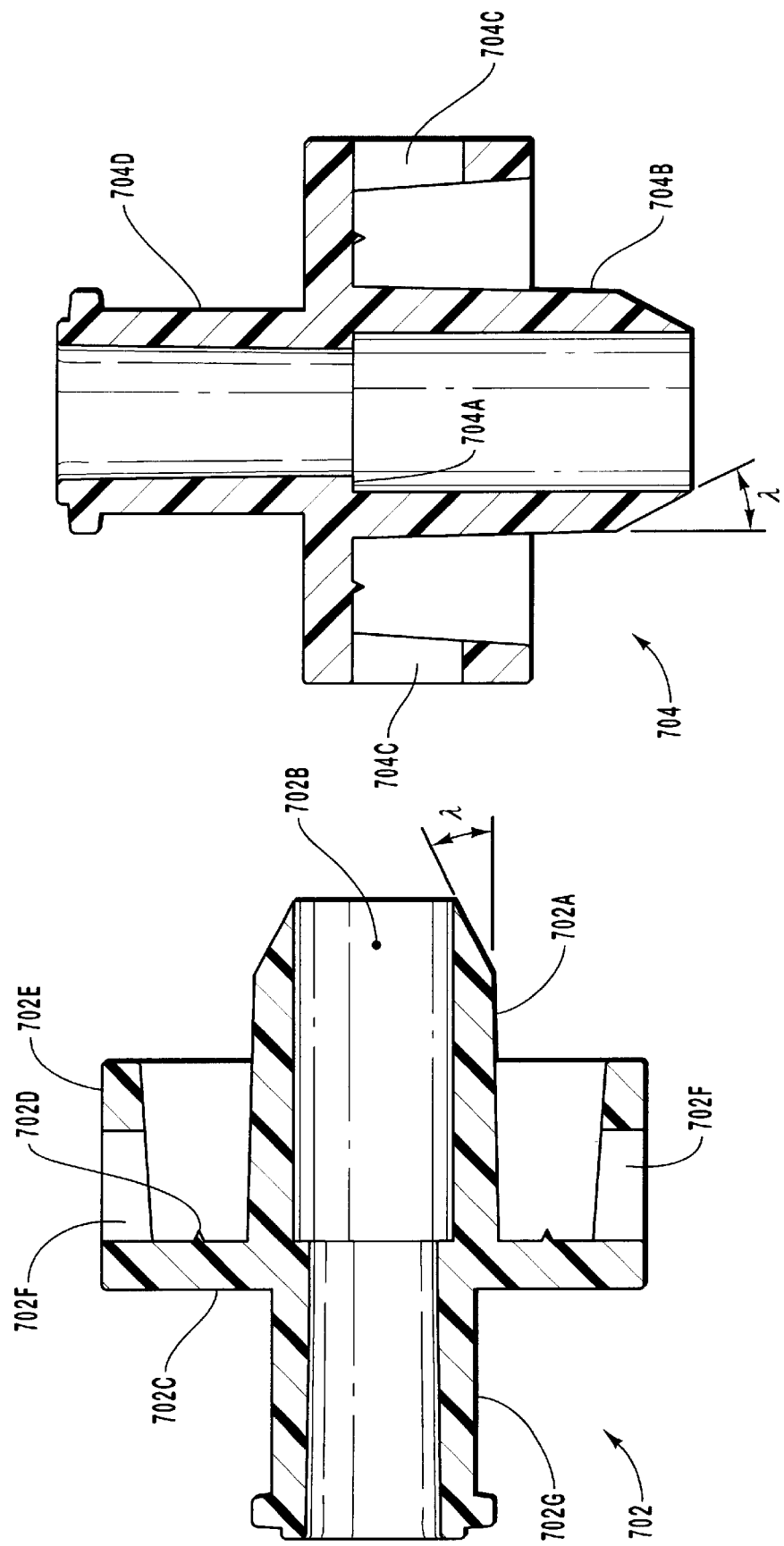
FIG. 11A is a cross section view of an embodiment of a fitting.
FIG. 11B is another cross section view of an embodiment of a fitting.

With particular reference to FIG. 11A, fitting 702 is substantially circular in shape and includes a nipple 702A defining a passageway 702B. A web 702C, disposed about nipple 702A, includes a seat 702D, preferably integral with web 702C, adapted to interact with flange 406 (FIG. 8) of insert 400 when fitting 702 is attached to housing 300. Disposed about web 702C is a flange 702E which, among other things, lends strength and rigidity to fitting 702. Additionally, flange 702E defines a plurality of slots 702F adapted to engage retention tabs 316 (FIG. 7) of housing 300 so as to facilitate permanent securement of fitting 702 to distal end 304 of housing 300. Finally, fitting 702 includes a hollow hub 702G which includes structure adapted to mate with various standardized medical devices and connectors. Preferably, hub 702G is adapted to mate with medical devices employing a Luer lock configuration. However, it will be appreciated that the structure of hub 702G may be modified and/or varied as required to suit contemporaneous use of a particular desired medical device.

Figure 12:
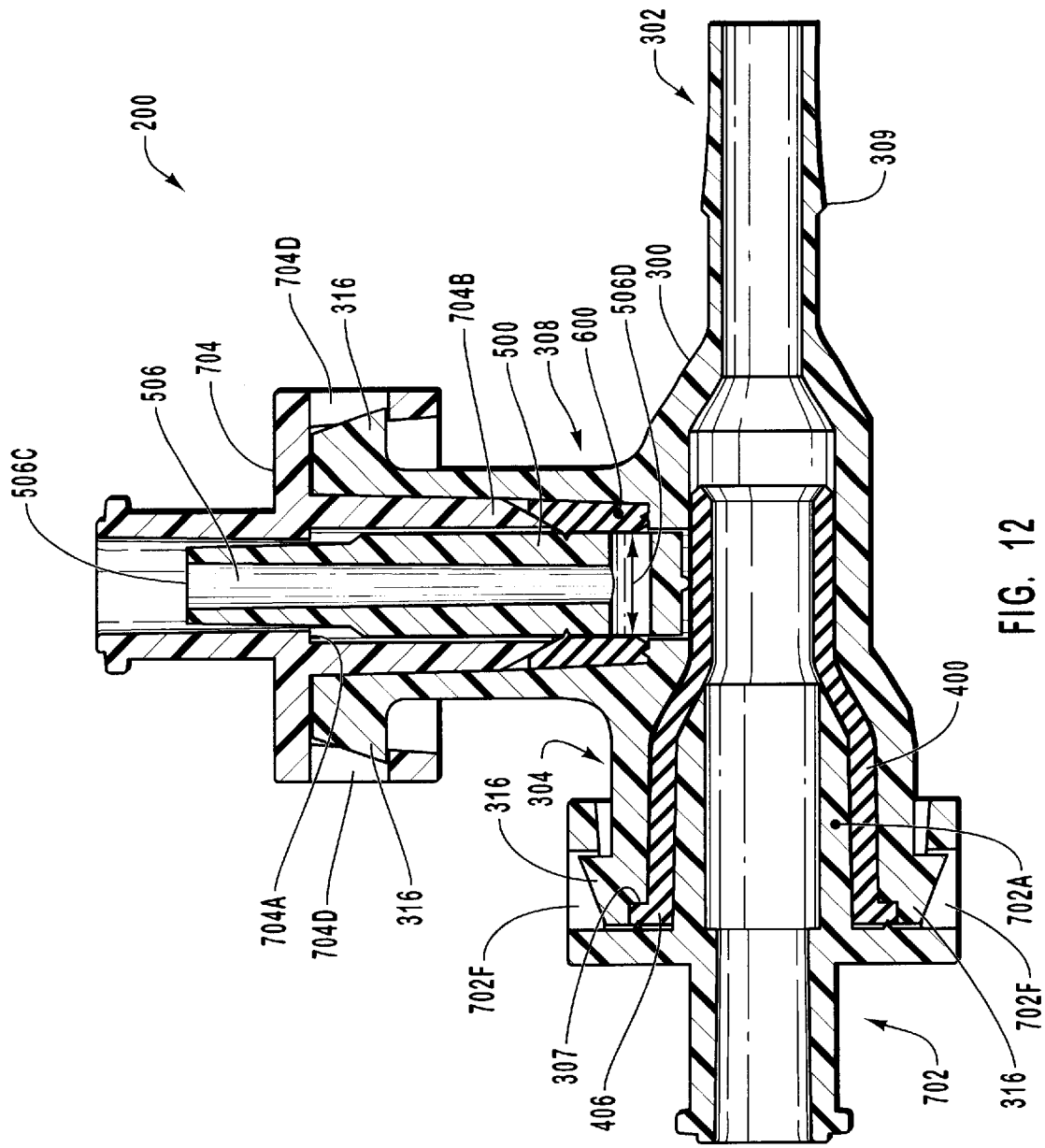
FIG. 12 is a cross section view of an embodiment of the valve apparatus with the plunger in the open position.
Figure 13:
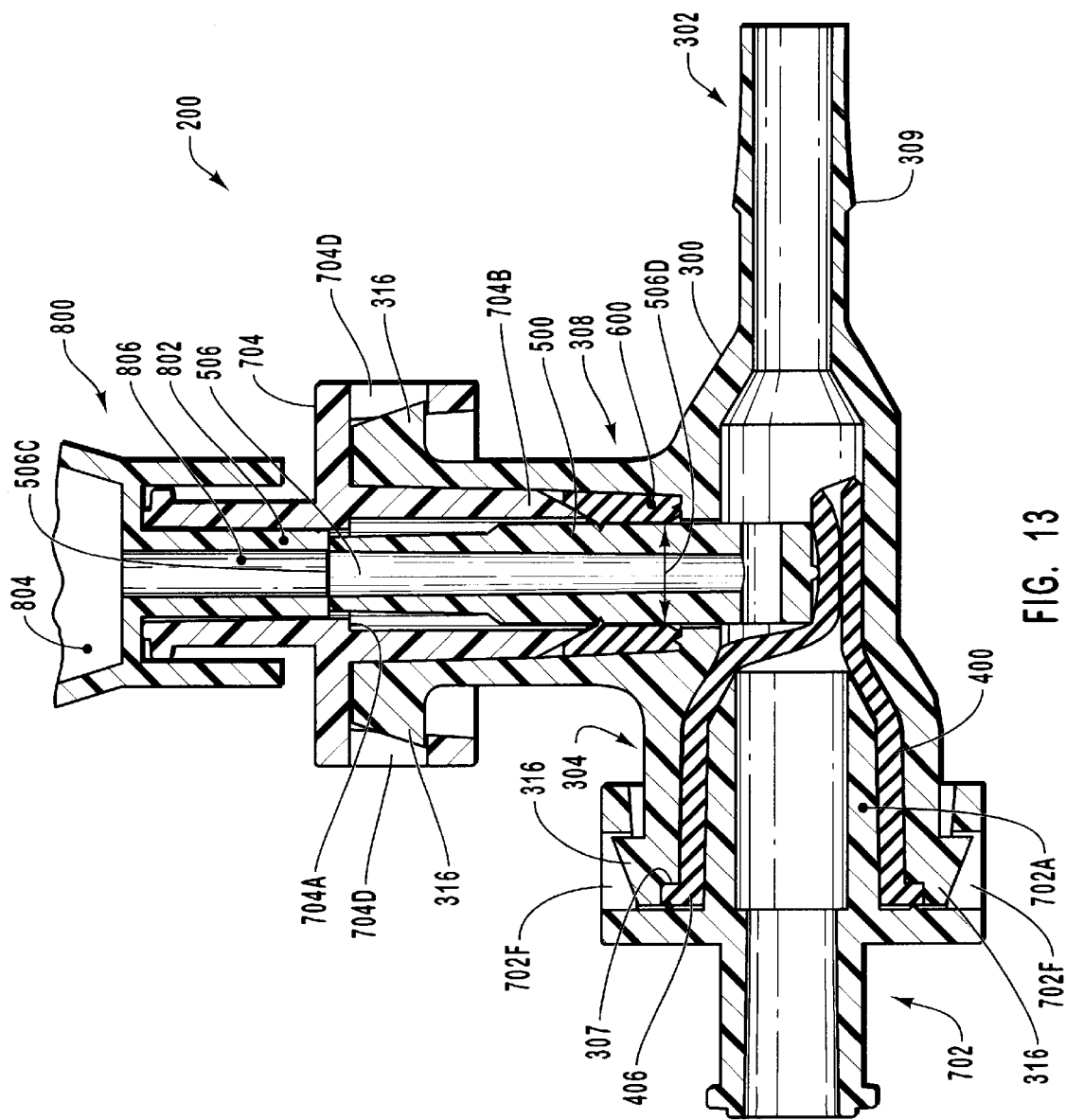
FIG. 13 is a cross section view of an embodiment of the valve apparatus with the plunger in the closed position.

Directing particular attention to nipple 702A, it will be appreciated that the terminal end of nipple 702A that is received in insert 400 is characterized by geometry compatible with the internal geometry of insert 400 (see FIGS. 12 and 13). Accordingly, the terminal end of nipple 702A preferably conforms to a transition angle λ so as to substantially conform with the internal geometry defined by insert 400. It will be appreciated that by constructing nipple 702A and insert 400 in this way, various benefits are realized. For example, transition angle λ helps ensure that the wall of insert 400 is not unduly pinched or gouged when plunger 500 is in the "closed" position. As another example, the aforementioned geometry ensures that fitting 702 applies pressure evenly along the wall of insert 400 so as to ensure substantial contact between nipple 702A and insert 400, and thereby facilitate the formation of a seal between fitting 702 and insert 400. Finally, nipple 702A prevents the collapse of insert 400 when plunger 500 moves to the "closed" position (discussed below), and thereby facilitates the automatic return of plunger 500 to the "open" position (discussed below) when a medical device is detached from fitting 704.

Directing attention now to FIG. 11B, discussion is provided specifically concerning various features of fitting 704. As noted above in the context of the discussion of fitting 702, fitting 702 and 704 are substantially identical. Accordingly, only those features of fitting 704 that are germane to its operation in the illustrated embodiment will be discussed. In addition to including the features discussed above in the context of fitting 702, fitting 704 additionally includes an annular shoulder 704A defined within nipple 704B that is adapted to abut shoulder 504 of plunger 500, thereby limiting the range of travel of plunger 500 when fitting 704 is attached to access port 308. As suggested elsewhere herein, nipple 704B of fitting 704 has an inside diameter substantially the same as inside diameter $D_2$ of sealing ring 600, so that fitting 704 slidingly receives plunger 500. Similar to fitting 702, fitting 704 includes a plurality of slots 704C adapted to receive retention tabs 316 (FIG. 8) of housing 300, and further includes a hollow hub 704D.

Directing attention now to FIGS. 12 and 13, additional details are provided regarding the assembly and operation of valve apparatus 200. It will be appreciated however, that the assembly procedure described herein is exemplary in nature and is not intended to be, nor should it be construed as, limiting in relation to the structure of the present invention. In general, valve apparatus 200 is assembled in accordance with the following procedure, however, various other methods of assembly may be suitable as well. First, insert 400 is pushed into housing 300 until flange 406 is seated in annular ring 307 defined at distal end 304 of housing 300. Nipple 702A of fitting 702 is then placed into insert 400 and fitting 702 pushed into insert 400 until such time as slots 702F in fitting 702 engage retention tabs 316 of housing 300. In this way, insert 400 is securely retained in position within housing 300. Further, because flange 406 of insert 400 is at least partially compressed by seat 702D (FIG. 11A) of fitting 702, an effective seal between fitting 702 and body 300 is achieved that serves to prevent liquid present in passageway 306 from leaking past fitting 702 into the surrounding environment.

With continuing attention to the assembly of valve apparatus 200, sealing ring 600 is placed into bore 310 defined by access port 308 and pushed downward until lower sealing surface 604 of sealing ring 600 engages seat 314 defined by housing 300. Next, plunger 500 is placed in bore 310 and pushed downward so as to pass at least partially into sealing ring 600. As a result, flushing passage inlet 506C of plunger 500 is aligned with bore 310 of access port 308, and plunger 500 comes into substantial contact with wiper rings 606 of sealing ring 600. Finally, the terminal end of nipple 704B of fitting 704 is placed into bore 310 and fitting 704 is pushed downward until the terminal end of nipple 704B contacts upper sealing surface 602 of sealing ring 600, so as to slightly compress sealing ring 600, and retention tabs 316 are received in slots 704C of fitting 704.

As a consequence of the placement of fitting 704 in this way, plunger 500 is trapped within valve apparatus 200 and the range of motion of plunger 500 is collectively defined by insert 400 and by annular shoulder 312, defined within bore 310 of access port 308. Further, nipple 704B of fitting 704 securely holds sealing ring 600 in position on seat 314 of housing 300 so that vertical motion of sealing ring 600 in bore 310 is substantially precluded. Additionally, as a result of the engagement of upper sealing surface 502 by fitting 704, leakage of materials in passage 306 past sealing ring 600 is substantially precluded. Finally, the resilience of insert 400 serves to bias plunger 500 upward to an "open" position wherein flushing passage outlets 506D are not in fluid communication with passage 306, and wherein fluid is substantially free to flow between proximal end 302 and distal end 304 of housing 300 of valve apparatus 200.

Thus, when plunger 500 is in the "open" position, insert 400, plunger 500, and sealing ring 600 collectively assume a "drain" mode of operation wherein valve apparatus 200 facilitates drainage of various fluids or other materials from, for example, a patient, by way of a catheter or the like attached to proximal end 302 of housing 300. The material passing through housing 300 from proximal end 302 then exits distal end 304 of housing 300 and passes into a collection device, such as a drainage bag or the like, that is in fluid communication with distal end 304.

Directing renewed attention now to FIG. 13, additional details are provided regarding various additional features of valve apparatus 200. In addition to the "open" position illustrated in FIG. 12, plunger 500 of valve apparatus 200 is also configured to assume a "closed" position wherein plunger 500 passes downward through sealing ring 600 and into passageway 306, with bulb 508 of plunger 500 substantially compressing at least a portion of insert 400 so that flow between proximal end 302 and distal end 304 of housing 300 is substantially precluded. At the same time as plunger 500 travels downward and pinches insert 400 shut, horizontal run 506B of flushing passage 506 defined by plunger 500 moves into fluid communication with proximal portion 306A of passageway 306.

Generally, plunger 500 is moved into the "closed" position by attachment of a medical device 800, preferably a syringe having a Luer lock configuration, to fitting 704. More particularly, medical device 800 includes structure 802 which fits within hub 704D (FIG. 11B) of fitting 704 and which serves to push plunger 500 downward into the "closed" position. At such time as medical device 800 has releasably engaged fitting 704, fluids or other materials present in chamber 804 of medical device 800 can then be directed downwards through passageway 806 of medical device, which is in fluid communication with flushing passage 506, and directed through flushing passage 506 and ultimately into passageway 306 of housing 300. Upon detachment of medical device 800, plunger 500 automatically moves upward, under the influence of the bias imposed by insert 400, until shoulder 504 is stopped by shoulder 312 defined in bore 310. As plunger 500 moves upward, wiper rings 606 of sealing ring 600 act to clean and seal the outer surface of plunger 500 during operation and to direct any removed material into horizontal run 506B of flushing passage 506.

Thus, when plunger 500 is in the "closed" position, insert 400, plunger 500, and sealing ring 600 collectively assume a "flush" mode of operation wherein valve apparatus 200 facilitates the introduction of flushing materials, such as antiseptics and the like, by way of access port 308, for use in flushing a drainage catheter or other medical device in fluid communication with proximal end 302 of housing 300.

It will be appreciated that a variety of other structures, and/or combinations thereof, may be profitably employed to perform the collective functions, enumerated herein, of insert 400, plunger 500, and sealing ring 600. Accordingly, insert 400, plunger 500, and sealing ring 600 collectively comprise but one example of a means for controlling flow. As discussed above, such a means for controlling flow preferably has at least first and second modes of operation, preferably a "flush" mode and a "drain" mode, respectively. It should be understood that the embodiments of insert 400, plunger 500, and sealing ring 600 are presented herein solely by way of example and should not be construed as limiting the scope of the present invention in any way.

While embodiments of the present invention are effective in performing flushing and draining procedures, it will be appreciated that when plunger 500 is in the closed position, valve apparatus 200 may alternatively be used to aspirate material through a medical device, such as a drainage tube or catheter, attached to proximal end 302 of housing 300. To implement such aspiration, a suction device (not shown), configured similarly to medical device 800, is attached to fitting 704 and suction is then applied. Materials aspirated as a result of the applied suction pass through proximal end 302 of housing 300 into flushing passage 506, and then out of valve apparatus 200 and into the suction, or other, device.

Figure 14:
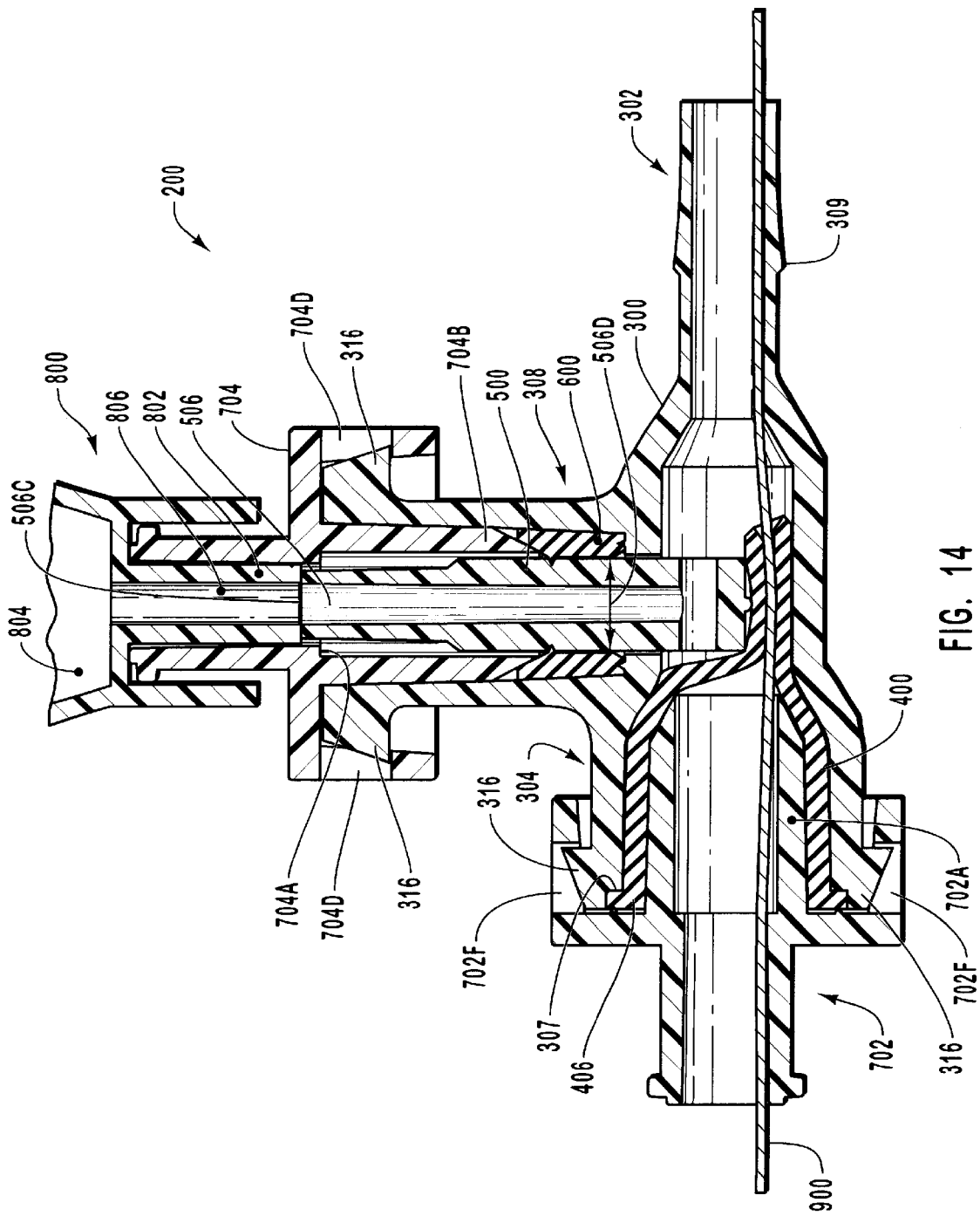
FIG. 14 is a cross section view of an embodiment of the valve apparatus used in conjunction with a medical instrument.

Further, it will be appreciated that, as indicated in the embodiment illustrated in FIG. 14, embodiments of the present invention are well suited for use in conjunction with diagnostic, analytical, therapeutic, and other procedures which require for their implementation medical instruments such as guidewires, endoscopic devices, and/or various other devices. Note that, as contemplated herein, "medical device" refers to any of a variety of components, including, but not limited to, drainage bags, catheters, drain tubes, and syringes, that can be connected either directly or indirectly with a valve apparatus 200. Further, "medical instrument" refers to such instruments and devices as may be passed, either partially or completely, through valve apparatus 200 so as to come into either direct or indirect contact with a patient.

Thus, as indicated in FIG. 14, flushing, or other medical procedures may be performed with valve apparatus 200 even while a medical instrument 900 is disposed within passageway 306 of housing 300 of valve apparatus 200. The resilience of insert 400 allows insert 400 to seal tightly around medical instrument 900 when plunger 500 is in the "closed" position. Further, because the diameter of passageway 306 is relatively large with respect to the diameter or thickness of medical instrument 900, the presence of medical instrument 900 in passage 306 presents no material impediment to flow therethrough, or to the operation of valve apparatus 200.

Thus, embodiments of the present invention include systems comprising, among other things, a valve apparatus 200 for use in conjunction with one or more medical instruments 900. Additionally, it will be appreciated that a plurality of valve apparatuses 200 may be employed, for example, either serially or in parallel, in a manifold, or other, configuration so as to facilitate substantially contemporaneous performance of a variety of procedures. Note that procedures performed by way of such a configuration may be performed either in conjunction with, or without, one or more medical devices 900. Such configurations are accordingly contemplated as being within the scope of the present invention.

Finally, while embodiments of the present invention are well suited for use in medical flushing-type applications, it will be appreciated that embodiments of the present invention may also be suitable for use in a variety of other contexts and procedures as well. Generally, embodiments of the present invention are suitable for use in any environment wherein the functionality disclosed herein would prove useful.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A valve apparatus for use in conjunction with at least one medical device, the valve apparatus comprising:
   (a) a housing having a passageway formed therethrough and said passageway having proximal and distal ends, said housing further comprising an access port having a bore formed therein;
   (b) a first fitting attached to said access port; and
   (c) an insert substantially disposed within said passageway;
   (d) a plunger slidingly disposed in said bore and having an open position wherein fluid is substantially free to flow between said proximal and distal ends of said passageway, and a closed position wherein fluid flow between said proximal and distal ends of said passageway is substantially prevented, said plunger assuming said closed position in response to attachment of the medical device to said first fitting and said plunger assuming said open position in response to detachment of the medical device from said first fitting, wherein in said closed position said plunger pinches a portion of said insert substantially shut so as to substantially prevent fluid flow between said proximal and distal ends of said passageway.

2. The valve apparatus as recited in claim 1, wherein said insert biases said plunger into said open position so that upon detachment of the medical device from said first fitting, said plunger moves automatically into said open position.

3. The valve apparatus as recited in claim 1, further comprising a second fitting attached to said proximal end of said housing.

4. The valve apparatus as recited in claim 3, wherein said first connector and said second connector are substantially identical.

5. The valve apparatus as recited in claim 1, wherein said plunger defines a flushing passage therethrough in fluid communication with said bore of said access port, fluid flow between said flushing passage and said proximal end of said passageway being substantially prevented when said plunger is in said open position, and said flushing passage moving into alignment with said proximal end of said passageway so as to facilitate establishment of a flow path between the medical device and said proximal end of said passageway when said plunger moves to said closed position.

6. The valve apparatus as recited in claim 5, wherein said flushing passage comprises a plurality of flushing passage outlets.

7. The valve apparatus as recited in claim 1, wherein said sealing ring includes at least one wiper ring in substantial contact with said plunger.

8. The valve apparatus as recited in claim 1, wherein said insert defines a passageway having first and second diameters.

9. The valve apparatus as recited in claim 1, wherein said insert has a flared proximal portion.

10. A valve apparatus for use in conjunction with a medical device, comprising:
    (a) a housing having a passageway formed therethrough and said passageway having proximal and distal ends, said housing further comprising an access port having a bore formed therein;
    (b) a first fitting attached to said access port;
    (c) an insert substantially disposed within said passageway; and
    (d) a plunger slidingly disposed in said bore and having an open position wherein fluid is substantially free to flow between said proximal and distal ends of said passageway, and a closed position wherein fluid flow between said proximal and distal ends of said passageway is substantially prevented, said plunger assuming said closed position in response to attachment of the medical device to said first fitting and said plunger assuming said open position in response to detachment of the medical device from said first fitting, wherein in said closed position said plunger pinches a portion of said insert substantially shut so as to substantially prevent fluid flow between said proximal and distal ends of said passageway, and said plunger having a flushing passage formed therethrough which communicates with said bore in said access port so as to facilitate establishment of fluid communication between the medical device and said proximal end of said passageway when said plunger is in said closed position.

11. The valve apparatus as recited in claim 10, further comprising a sealing ring disposed within said bore so that at least a portion of said plunger resides within said sealing ring.

12. The valve apparatus as recited in claim 10, further comprising a second fitting attached to said housing at said proximal end of said passageway.

13. The valve apparatus as recited in claim 10, wherein said insert biases said plunger into said open position so that upon detachment of the medical device from said first fitting, said plunger moves automatically into said open position.

14. A valve apparatus for use in conjunction with a medical device, the valve apparatus comprising:
    (a) a housing having a passageway formed therethrough and said passageway having proximal and distal ends, said housing further comprising an access port having a bore formed therein;
    (b) a first fitting attached to said access port; and
    (c) a means for controlling fluid flow, said means for controlling fluid flow permitting fluid flow between said bore and said proximal end of said passageway when said means for controlling fluid flow is in a first operational mode, and said means for controlling fluid flow permitting fluid flow between said proximal and distal ends of said passageway when said means for controlling fluid flow is in a second operational mode.

15. The valve apparatus as recited in claim 14, wherein said first operational mode comprises a flush mode.

16. The valve apparatus as recited in claim 14, wherein said second operational mode comprises a drain mode.

17. The valve apparatus as recited in claim 14, wherein when said means for controlling fluid flow is in said first operational mode, said means for controlling fluid flow substantially prevents fluid flow between said proximal and distal ends of said passageway.

18. The valve apparatus as recited in claim 14, wherein when said means for controlling fluid flow assumes said first operational mode in response to attachment of the medical device to said first fitting.

19. The valve apparatus as recited in claim 14, wherein when said means for controlling fluid flow assumes said second operational mode in response to detachment of the medical device from said first fitting.

20. The valve apparatus as recited in claim 14, wherein when said means for controlling fluid flow comprises an insert disposed in said passageway, a sealing ring disposed in said bore, and a plunger slidingly disposed in said bore and at least partially residing in said sealing ring, and said plunger having an open position wherein fluid is substantially free to flow between said proximal and distal ends of said passageway, and a closed position wherein fluid flow between said proximal and distal ends of said passageway is substantially prevented, said plunger assuming said closed position in response to attachment of the medical device to said first fitting and said plunger assuming said open position in response to detachment of the medical device from said first fitting, wherein in said closed position said plunger pinches a portion of said insert substantially shut so as to substantially prevent fluid flow between said proximal and distal ends of said passageway.

21. The valve apparatus as recited in claim 20, wherein said plunger defines a flushing passage therethrough in fluid communication with said bore of said access port, fluid flow between said flushing passage and said proximal end of said passageway being substantially prevented when said plunger is in said open position, and said flushing passage moving into alignment with said proximal end of said passageway so as to facilitate establishment of a flow path between the medical device and said proximal end of said passageway when said plunger moves to said closed position.

22. A system for use in implementing medical procedures, the system comprising:
(a) a first medical device;
(b) at least one valve apparatus, including:
  (i) a housing having a passageway formed therethrough and said passageway having proximal and distal ends, said housing further comprising an access port having a bore formed therein;
  (ii) a first fitting attached to said access port;
  (iii) an insert substantially disposed within said passageway; and
  (iv) a plunger slidingly disposed in said bore and having an open position wherein fluid is substantially free to flow between said proximal and distal ends of said passageway, and a closed position wherein fluid flow between said proximal and distal ends of said passageway is substantially prevented, said plunger assuming said closed position in response to attachment of said first medical device to said first fitting and said plunger assuming said open position in response to detachment of said first medical device from said first fitting, wherein in said closed position said plunger pinches a portion of said insert substantially shut so as to substantially prevent fluid flow between said proximal and distal ends of said passageway;
(c) a second medical device in fluid communication with said proximal end of said passageway; and
(d) a medical instrument at least partially disposed within said passageway.

23. The system as recited in claim 22, wherein said first medical device comprises a syringe.

24. The system as recited in claim 22, wherein said second medical device is selected from the group consisting of: drainage tubes, and catheters.

25. The system as recited in claim 22, wherein said medical instrument is selected from the group consisting of: guide wires, and endoscopic devices.

26. The system as recited in claim 22, wherein said plunger defines a flushing passage therethrough in fluid communication with said bore of said access port, fluid flow between said flushing passage and said proximal end of said passageway being substantially prevented when said plunger is in said open position, and said flushing passage moving into alignment with said proximal end of said passageway so as to facilitate establishment of a flow path between the medical device and said proximal end of said passageway when said plunger moves to said closed position.

27. A system for use in implementing medical procedures, the system comprising:
(a) at least one medical device; and
(b) a manifold including a plurality of valve apparatuses arranged in a predetermined configuration, each valve apparatus comprising:
  (i) a housing having a passageway formed therethrough and said passageway having proximal and distal ends, said housing further comprising an access port having a bore formed therein;
  (ii) a first fitting attached to said access port;
  (iii) an insert substantially disposed within said passageway; and
  (iv) a plunger slidingly disposed in said bore and having an open position wherein fluid is substantially free to flow between said proximal and distal ends of said passageway, and a closed position wherein fluid flow between said proximal and distal ends of said passageway is substantially prevented, said plunger assuming said closed position in response to attachment of said at least one medical device to said first fitting and said plunger assuming said open position in response to detachment of said at least one medical device from said first fitting, wherein in said closed position said plunger pinches a portion of said insert substantially shut so as to substantially prevent fluid flow between said proximal and distal ends of said passageway.

28. The system as recited in claim 27, further comprising a medical instrument at least partially disposed within a passageway of one of said valve apparatuses.

29. The system as recited in claim 27, wherein said plunger defines a flushing passage therethrough in fluid communication with said bore of said access port, fluid flow between said flushing passage and said proximal end of said passageway being substantially prevented when said plunger is in said open position, and said flushing passage moving into alignment with said proximal end of said passageway so as to facilitate establishment of a flow path between the medical device and said proximal end of said passageway when said plunger moves to said closed position.

30. The system as recited in claim 27, wherein said at least one medical device comprises a syringe.

31. A drainage system for use in medical applications, the drainage system comprising:

(a) a first medical device;

(b) a valve apparatus, including:
- (i) a housing having a passageway formed therethrough and the passageway having proximal and distal ends, said housing further comprising an access port having a bore formed therein;
- (ii) a fitting attached to said access port;
- (iii) an insert substantially disposed within said passageway; and
- (iv) a plunger slidingly disposed in said bore and having at least an open position wherein fluid is substantially free to flow between said proximal and distal ends of said passageway and a closed position wherein fluid flow between said proximal and distal ends of said passageway is substantially prevented, said plunger assuming said closed position in response to attachment of said first medical device to said fitting and said plunger assuming said open position in response to detachment of said first medical device from said fitting, wherein in said closed position said plunger pinches said tubing substantially shut so as to substantially prevent fluid flow between said proximal and distal ends of said passageway;

(c) a catheter in fluid communication with said proximal end of said passageway;

(d) a drainage tube in fluid communication with said distal end of said passageway; and (e) a drainage reservoir in fluid communication with said drainage tube.

32. The drainage system as recited in 31, wherein said first medical device comprises a syringe.

33. The drainage system as recited in claim 31, wherein said plunger defines a flushing passage therethrough in fluid communication with said bore of said access port, fluid flow between said flushing passage and said proximal end of said passageway being substantially prevented when said plunger is in said open position, and said flushing passage moving into alignment with said proximal end of said passageway so as to facilitate establishment of a flow path between the medical device and said proximal end of said passageway when said plunger moves to said closed position.

34. The drainage system as recited in claim 31, further comprising a sealing ring disposed within said bore so that at least a portion of said plunger resides within said sealing ring.

\* \* \* \* \*